United States Patent
Birk et al.

(10) Patent No.: US 8,007,465 B2
(45) Date of Patent: *Aug. 30, 2011

(54) IMPLANTABLE DEVICE FASTENING SYSTEM AND METHODS OF USE

(75) Inventors: Janel A. Birk, Oxnard, CA (US); Frederick L. Coe, Santa Barbara, CA (US); Robert E. Hoyt, Santa Barbara, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/488,496

(22) Filed: Jun. 19, 2009

(65) Prior Publication Data

US 2009/0259231 A1 Oct. 15, 2009

Related U.S. Application Data

(63) Continuation of application No. 10/562,964, filed as application No. PCT/US2004/030053 on Sep. 15, 2004, now Pat. No. 7,762,998.

(60) Provisional application No. 60/503,074, filed on Sep. 15, 2003, provisional application No. 60/538,674, filed on Jan. 23, 2004.

(51) Int. Cl.
*A61M 5/00* (2006.01)
(52) U.S. Cl. ........................................ 604/110
(58) Field of Classification Search ............... 604/93.01, 604/175, 288.01; 606/217, 213, 219, 139
See application file for complete search history.

(56) References Cited

U.S. PATENT DOCUMENTS

| | | | |
|---|---|---|---|
| 3,371,352 A | 3/1968 | Siposs et al. | |
| 3,587,115 A | 6/1971 | Shiley | |
| 3,840,018 A | 10/1974 | Heifetz | |
| 4,118,805 A | 10/1978 | Reimels | |
| 4,413,985 A | 11/1983 | Wellner | |
| 4,692,146 A | 9/1987 | Hilger | |
| 4,696,288 A | 9/1987 | Kuzmak | |
| 4,760,837 A | 8/1988 | Petit | |
| 4,762,517 A | 8/1988 | McIntyre | |
| 4,781,680 A | 11/1988 | Redmond | |
| 4,892,518 A | 1/1990 | Cupp | |
| 4,978,338 A | 12/1990 | Melsky | |
| 5,006,115 A | 4/1991 | McDonald | |

(Continued)

FOREIGN PATENT DOCUMENTS
WO    WO 9926543 A1    6/1999

OTHER PUBLICATIONS

U.S. Appl. No. 60/478,763, filed Jun. 16, 2003, Conlon.

*Primary Examiner* — Nicholas D Lucchesi
*Assistant Examiner* — Diva Ranade
(74) *Attorney, Agent, or Firm* — Stephen Donovan; Debra Condino

(57) ABSTRACT

A surgical fastening system for implantable devices is disclosed. The implantable device may contain a plurality of fasteners in pre-deployment position, may have a housing fitted over or around it which contains a plurality of fasteners in pre-deployment position, or may be a part of a two-part system into which it fits. Accordingly, the present invention also encompasses a deployment system or tool that optionally positions the implantable device, and which causes the fasteners to move into post-deployment position. The fasteners may be staples, metal loops, coils, springs or hooks formed of biocompatible materials, including shape memory alloys such as NiTi.

16 Claims, 31 Drawing Sheets

U.S. PATENT DOCUMENTS

| | | |
|---|---|---|
| 5,074,868 A | 12/1991 | Kuzmak |
| 5,092,897 A | 3/1992 | Forte |
| 5,188,609 A | 2/1993 | Bayless |
| 5,207,644 A | 5/1993 | Strecker |
| 5,263,930 A | 11/1993 | Ensminger |
| 5,391,156 A | 2/1995 | Hildwein |
| 5,449,368 A | 9/1995 | Kuzmak |
| 5,540,648 A | 7/1996 | Yoon |
| 5,607,418 A | 3/1997 | Arzbaecher |
| 5,653,718 A | 8/1997 | Yoon |
| 5,688,247 A | 11/1997 | Haindl |
| 5,718,682 A | 2/1998 | Tucker |
| 5,728,116 A | 3/1998 | Rosenman |
| 5,769,877 A | 6/1998 | Barreras |
| 5,833,698 A | 11/1998 | Hinchcliffe |
| 5,871,532 A | 2/1999 | Schroepel |
| RE36,176 E | 3/1999 | Kuzmak |
| 5,910,149 A | 6/1999 | Kuzmak |
| 5,928,195 A | 7/1999 | Malamud |
| 5,944,696 A | 8/1999 | Bayless |
| 5,989,216 A | 11/1999 | Johnson |
| 6,048,309 A | 4/2000 | Flom |
| 6,074,341 A | 6/2000 | Anderson |
| 6,102,922 A | 8/2000 | Jakobsson |
| 6,106,550 A | 8/2000 | Magovern |
| 6,193,734 B1 | 2/2001 | Bolduc |
| 6,254,642 B1 | 7/2001 | Taylor |
| 6,419,696 B1 | 7/2002 | Ortiz |
| 6,443,957 B1 | 9/2002 | Addis |
| 6,453,907 B1 | 9/2002 | Forsell |
| 6,454,699 B1 | 9/2002 | Forsell |
| 6,461,293 B1 | 10/2002 | Forsell |
| 6,475,136 B1 | 11/2002 | Forsell |
| 6,478,783 B1 | 11/2002 | Moorehead |
| 6,485,496 B1 | 11/2002 | Suyker |
| 6,517,556 B1 | 2/2003 | Monassevitch |
| 6,565,582 B2 | 5/2003 | Gifford |
| 6,676,674 B1 | 1/2004 | Dudai |
| 6,766,186 B1 | 7/2004 | Hoyns |
| 6,966,875 B1 | 11/2005 | Longobardi |
| 7,144,400 B2 | 12/2006 | Byrum |
| 7,191,007 B2 | 3/2007 | Desai |
| 7,195,774 B2 | 3/2007 | Decarvalho et al. |
| 7,282,023 B2 | 10/2007 | Frering |
| 7,311,716 B2 | 12/2007 | Byrum |
| 7,338,433 B2 | 3/2008 | Coe |
| 7,341,577 B2 | 3/2008 | Gill |
| 7,351,198 B2 | 4/2008 | Byrum |
| 7,351,240 B2 | 4/2008 | Hassler |
| 7,353,747 B2 | 4/2008 | Swayze |
| 7,364,542 B2 | 4/2008 | Jambor |
| 7,367,937 B2 | 5/2008 | Jambor |
| 7,374,557 B2 | 5/2008 | Conlon |
| 7,374,565 B2 | 5/2008 | Hassler |
| 7,390,294 B2 | 6/2008 | Hassler |
| 7,416,528 B2 | 8/2008 | Crawford |
| 7,481,763 B2 | 1/2009 | Hassler |
| 2003/0045902 A1 | 3/2003 | Weadock |
| 2003/0066536 A1 | 4/2003 | Forsell |
| 2003/0158564 A1 | 8/2003 | Benchetrit |
| 2003/0208212 A1 | 11/2003 | Cigaina |
| 2004/0153106 A1 | 8/2004 | Dudai |
| 2004/0254537 A1 | 12/2004 | Conlon |
| 2005/0070937 A1 | 3/2005 | Jambor |
| 2005/0131352 A1 | 6/2005 | Conlon |
| 2005/0148956 A1 | 7/2005 | Conlon |
| 2005/0192531 A1 | 9/2005 | Birk |
| 2005/0192601 A1 | 9/2005 | Demarais |
| 2005/0240155 A1 | 10/2005 | Conlon |
| 2005/0277899 A1 | 12/2005 | Conlon |
| 2005/0283118 A1 | 12/2005 | Uth |
| 2005/0283119 A1 | 12/2005 | Uth |
| 2006/0173424 A1 | 8/2006 | Conlon |
| 2006/0178647 A1 | 8/2006 | Stats |
| 2006/0217673 A1 | 9/2006 | Schulze |
| 2007/0078391 A1 | 4/2007 | Wortley |
| 2007/0088391 A1 | 4/2007 | McAlexander |
| 2007/0161958 A1 | 7/2007 | Glenn |

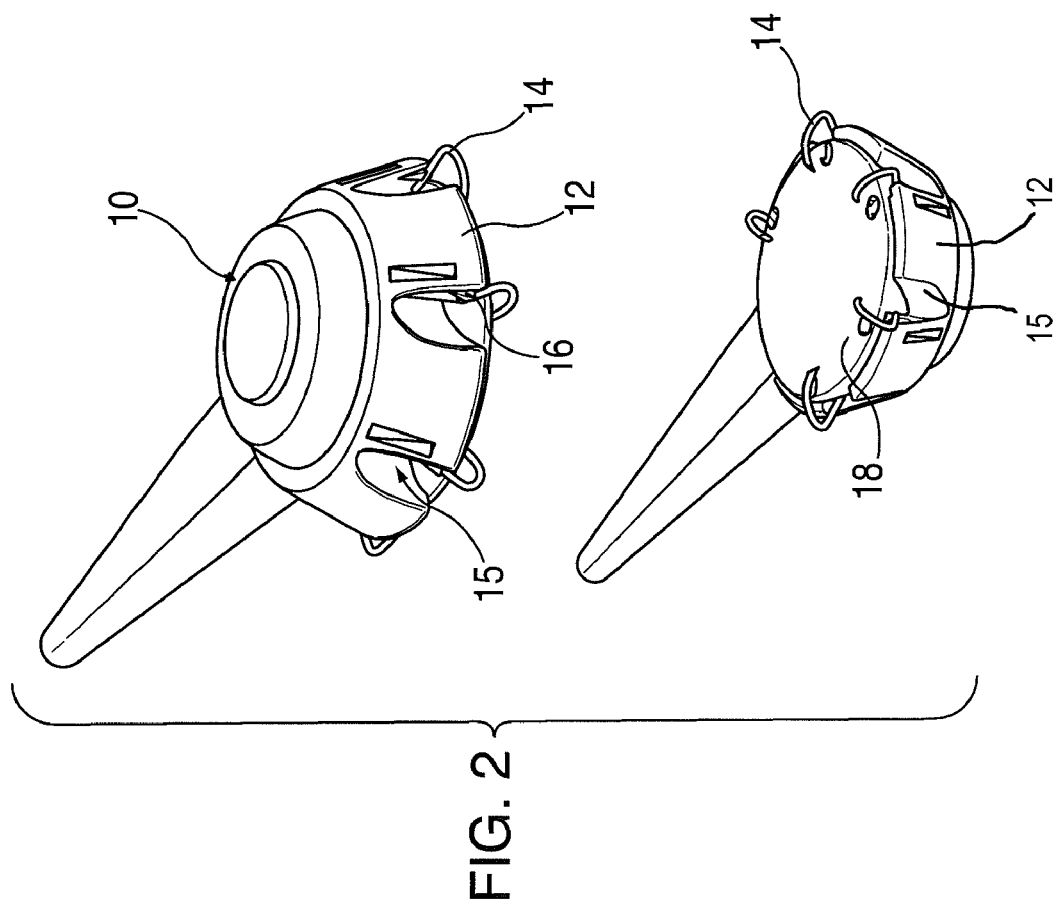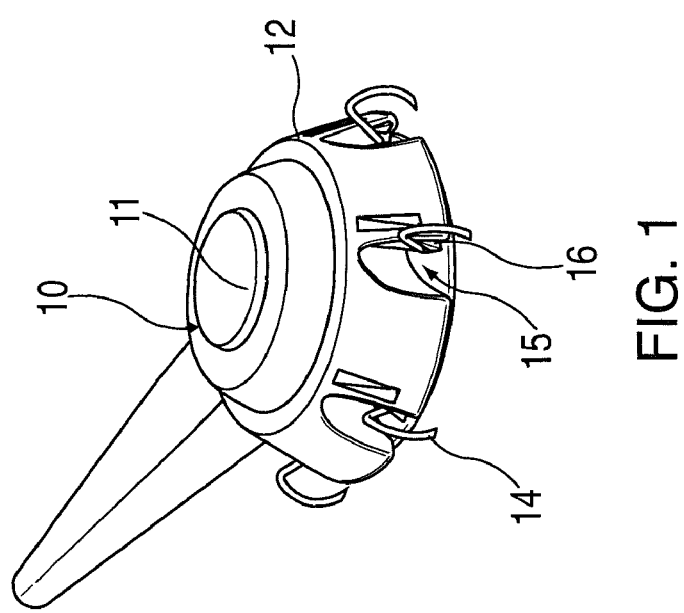

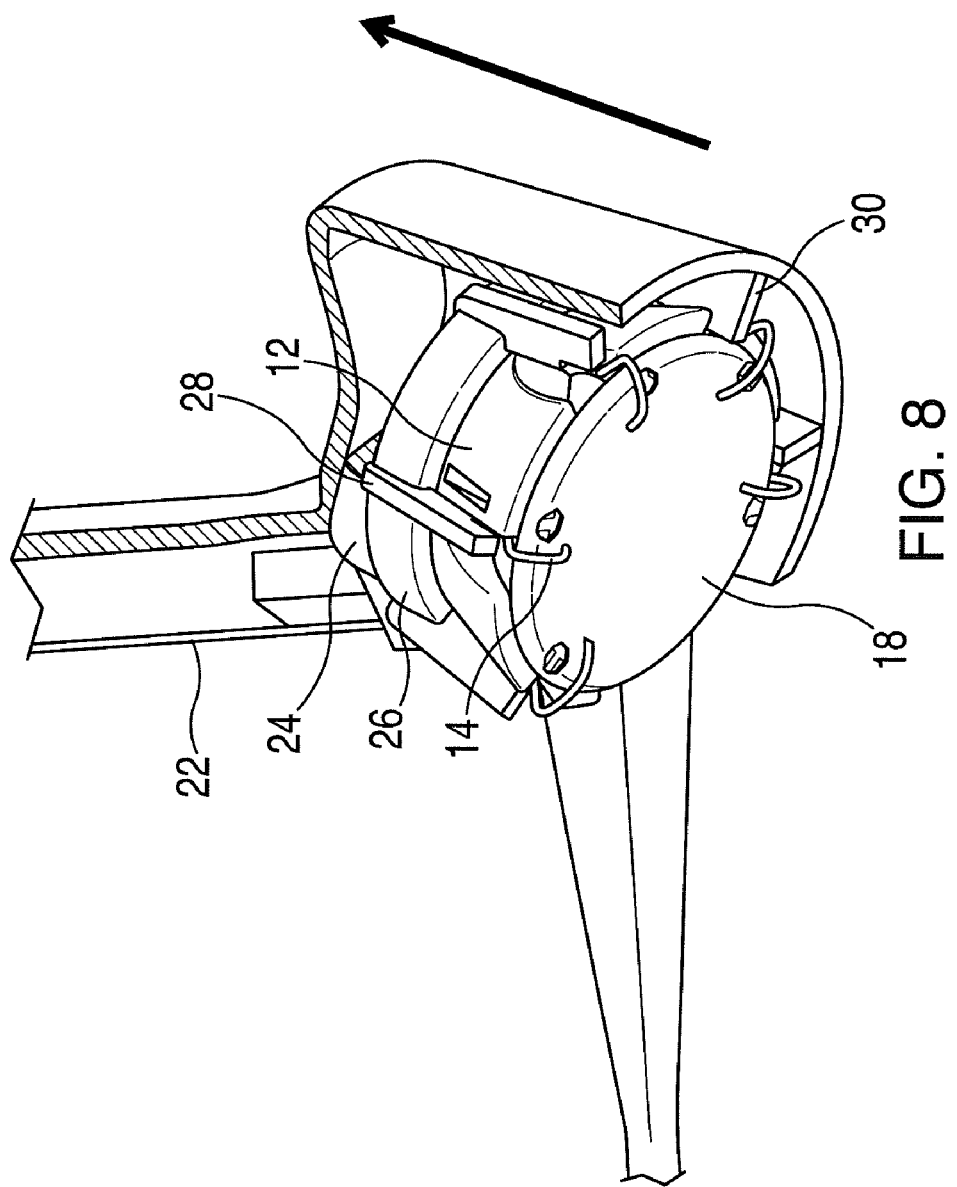

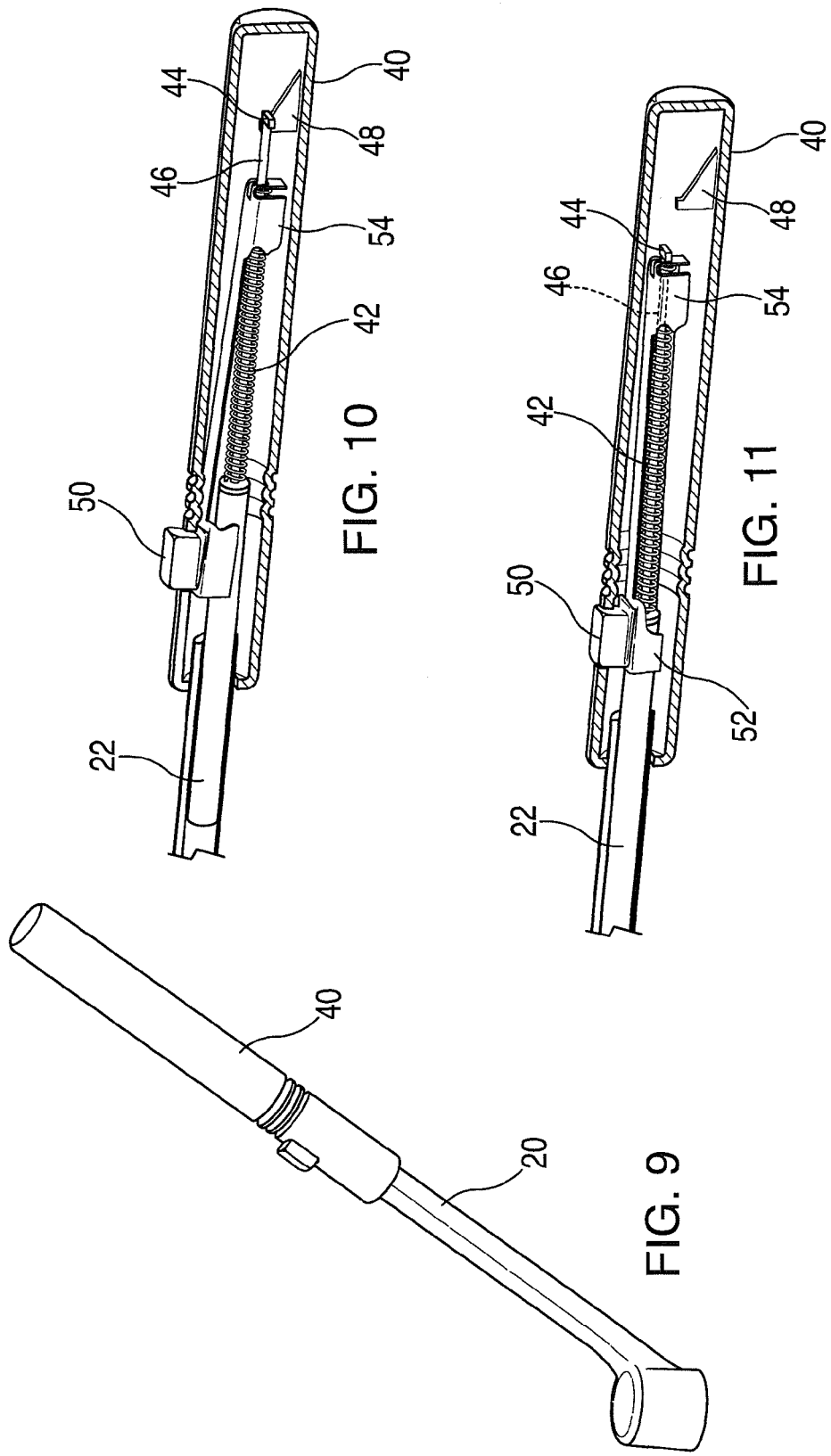

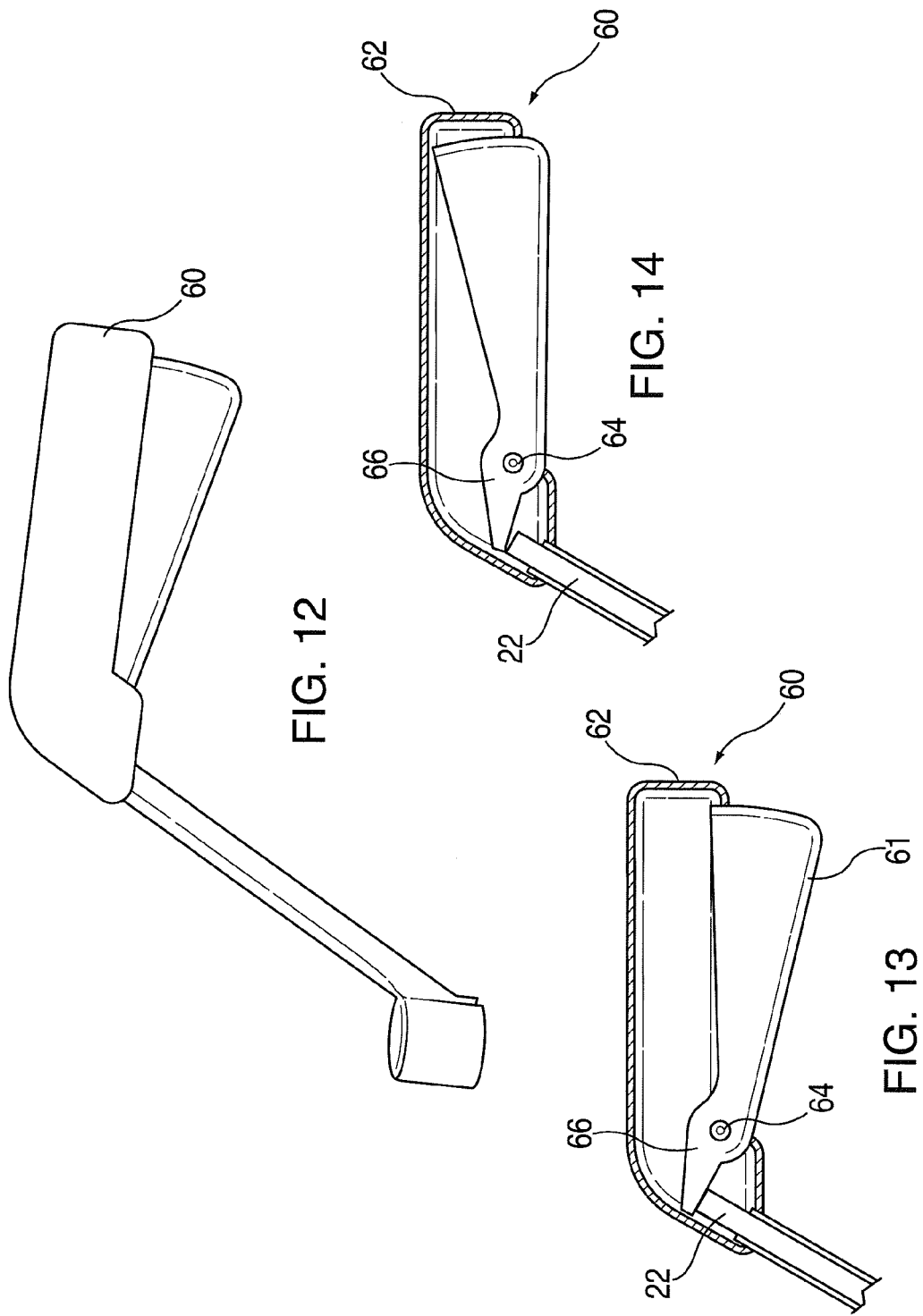

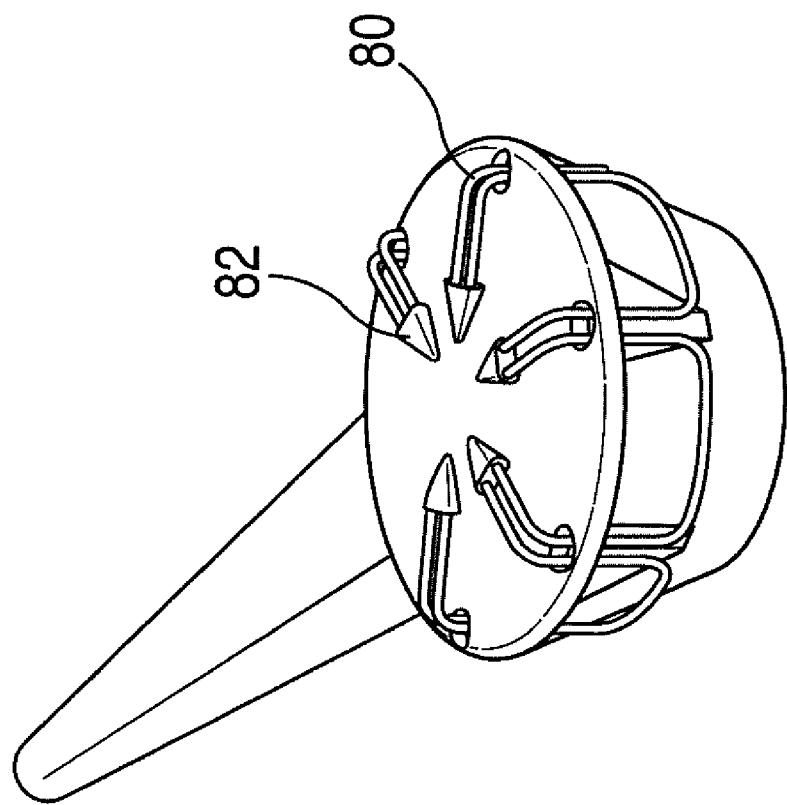

IMPLANTABLE DEVICE FASTENING SYSTEM AND METHODS OF USE

RELATED APPLICATIONS

The present application is a continuation of U.S. application Ser. No. 10/562,964, having a 35 U.S.C. §371 date of Dec. 30, 2005 now U.S. Pat. No. 7,762,998 as a National stage application of PCT/US04/30053, filed Sep. 15, 2004, which claims priority to U.S. Provisional Application No. 60/503,074 filed Sep. 15, 2003 and to U.S. Provisional Application No. 60/538,674 filed Jan. 23, 2004, each of which is incorporated herein by reference in its entirety.

FIELD OF THE INVENTION

The present invention relates to the fields of implantable medical devices and surgical instruments and fasteners. The present invention encompasses methods of fastening devices or implants in surgical procedures and the surgical fasteners and instruments used in the process.

BACKGROUND OF THE INVENTION

Surgical fasteners such as staples, clips, clamps, bands, tacks, or other wound or incision closure devices are commonly used in surgical procedures to allow a surgeon to fasten, secure and/or repair body tissue. Examples of surgical fasteners are given in U.S. Pat. Nos. 4,994,073 or 4,950,284 or 4,934,364 and 4,932,960.

Surgical fasteners have been used in surgical procedures to eliminate the need for suturing, which is both time consuming and inconvenient. In these applications the surgeon often uses a fastener implanting device loaded with one or more surgical fasteners to accomplish in a few seconds what would have taken many minutes to perform by suturing. This reduction in operating time reduces blood loss and trauma to the patient.

Typically, such fastening systems have been used mainly for the closure of incisions or wounds, or to fasten tissues together. A surgical fastening system that could be used with a number of types of implantable devices would be beneficial for surgeons. Currently, surgical devices that incorporate fastening systems often use extremely specialized systems that may be unnecessarily complicated and are unsuitable for adaptation to other applications. As a result, the majority of implantable devices are secured with sutures. For example, when inserting a gastric band and the associated access port, the port is sutured into place with 4 to 5 sutures against the rectus muscle sheath. Such placement of the sutures is often challenging because the ports are placed below several inches of fat, and suturing the port often takes as long as placing the band itself. An improved fastening system would allow easy, one-step attachment with security equivalent to the sutured device.

The present invention overcomes such problems in the art.

SUMMARY OF THE INVENTION

The present invention encompasses surgical fastening systems wherein an implantable device either contains a plurality of fasteners in pre-deployment position, or wherein an implantable device may have a housing fitted over the device, wherein the housing contains a plurality of fasteners in pre-deployment position. Accordingly, the present invention also encompasses a deployment system that optionally positions the implantable device, and which causes the fasteners to move into post-deployment position.

BRIEF DESCRIPTION OF THE DRAWINGS

The above objects and advantages of the present invention will be more fully understood by reference to the following description and annexed drawings, in which:

FIG. 1 is a top perspective view of a radial pivot fastener with staples in pre-deployment positions;

FIG. 2 shows top and bottom perspective views of the radial pivot fastener of FIG. 1 with staples in deployed positions; the top view shows the staples locked-out in the deployed position, while the bottom view shows the staples nested against the bottom of port which is thus "sandwiched" between a housing ring and the staples;

FIG. 8 is a detail cutaway elevation view of the distal end of the delivery system of FIG. 6 and a port fastener in deployment position;

FIG. 9 is an elevation view of a pencil grip handle configuration for a delivery system;

FIG. 10 is a detail cutaway elevation view of the handle of the delivery system of FIG. 9 shown in a starting position;

FIG. 11 is a detail cutaway elevation view of the handle of the delivery system of FIG. 9 shown in a fired position;

FIG. 12 is an elevation view of a pistol grip handle configuration for a delivery system;

FIG. 13 is a detail elevation view of the handle of the delivery system of FIG. 12 shown in a starting position;

FIG. 14 is a detail elevation view of the handle of the delivery system of FIG. 12 shown in a fired position;

FIG. 24 is a bottom elevation view of a molded tip continuous wire form fastener;

DETAILED DESCRIPTION OF THE PREFERRED EMBODIMENTS

Figure 4:
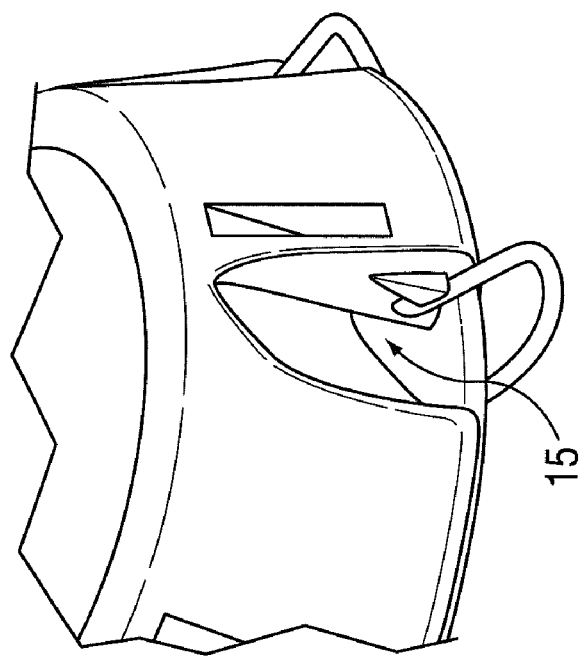
FIG. 4 is a detail elevation view of the radial pivot fastener of FIG. 2 with staples in deployment position.

The present invention encompasses surgical fastening systems wherein an implantable device either contains a plurality of fasteners (e.g. staples) in pre-deployment position, or wherein fasteners are provided adapted to suture holes on the device, or wherein an implantable device may have a detachable housing fitted over the device, wherein the housing contains a plurality of fasteners in pre-deployment position.

The detachable housing and fasteners may be made of various materials known in the art for the manufacture of surgical fasteners and implants. The fasteners may be made of metal, polymer, or other suitable materials. The detachable housing may be made of metal, polymer, ceramic, or composites; for instance polysulfone, acetyl copolymers, titanium, elastomers and stainless steel are commonly used.

These materials must be biocompatible, i.e., they do not adversely affect the surrounding living environment, and conversely, their performance is not adversely affected by the surrounding living environment. The materials may be inert non-absorbable or biodegradable. Inert materials may be fairly indestructible and maintain their form and function for extended periods of time.

Metals and metal alloys, and particularly titanium and titanium alloys, are used for a great variety of implantable articles for medical applications. All implantable articles suffer from some degree of bio-incompatibility, which may be manifested as tissue inflammation, necrosis, hyperplasia, mutagenicity, toxicity, and other reactions, such as attack by giant cells, leukocytes and macrophages. While titanium and its alloys are generally considered inert when implanted, some biological and biochemical interactions still may occur, and others have found it desirable to provide various coatings on the surface of titanium and titanium alloy implants for certain purposes. The same holds true for many other metals and metal alloys. Thus, the present invention encompasses the use of such coatings on the surface of the fasteners, the removable housing, or the device.

Some of the coatings that may be used in materials to be implanted (whether made of titanium or other materials) include biological agents (such as genetic material or cellular material) or chemical agents (such as anti-proliferation reagents or cell-growth factors) to reduce problems associated with hyperplasia or inflammation. These agents may be mixed with binders such as elastomers or bio-resorbable polymers to the surface of a metal or polymer object.

The fasteners contemplated herein, including staples, are often constructed of wire and thus have a relatively large surface area for their size. Accordingly, methods that allow the addition of biological and biochemical agents to the surface of the implant may be advantageous in minimizing the adverse reactions of body tissues with the implant. These may include coatings applied to stainless steel and titanium alloys (e.g., NiTi alloys) to retard tissue reactions. Such coatings have been based upon stable bio-compatible polymers (such as styrene-isobutylene-styrene (SIBS)) and bio-resorbable polymers, such as polyglycolic acid. In the work known to date, the active chemical or biological agent is mixed with the polymeric coating material, and the agent then elutes from the coating once the implant is placed in the body.

It is also contemplated by the present invention that the fasteners may be made of shape memory alloy (SMA). The driving force for making metal medical devices from shape memory alloys lies in their great resistance to permanent deformation as compared to conventional alloys employed in this application. Alloys used in various medical instruments have relied on stainless steel, high nickel alloys such as Elgiloy™ and titanium based alloys, all of which can be given quite high yield strength through work hardening. Normal metals, even with very high yield strength, cannot sustain strains much greater than 0.2% without suffering a permanent set. Once a bend or kink has been sustained in a device fabricated from one of the above conventional alloys it is virtually impossible to remove. The unusual property of pseudoelasticity exhibited by shape memory alloys such as Au—Cd, Cu—Zn—Al, Ni—Ti and many others makes possible the complete "elastic" recovery of strains as great as 10%. Due to its high recoverable strain and its excellent resistance to corrosion, the shape memory alloy of preference for medical components has been within the Ni—Ti family of alloys.

Shape memory alloys belong to a class which exhibit thermoelastic martensite transformation. The term martensite refers to the crystalline phase which is produced in steels when quenched from a high temperature. The phase which exists at the elevated temperature is referred to as austenite; these terms have been carried over to describe the transformations which occur in shape memory alloys. When a steel has been quenched from the austenitic temperature to martensite, to again form austenite requires heating the structure to quite high temperatures, usually in excess of 1400° F.

By contrast, the thermoelastic shape memory alloys can change from martensite to austenite and back again on heating and cooling over a very small temperature range, typically from 18 to 55° F. The transformation of a shape memory alloy is usually described by a hysteresis curve in which it is shown that on cooling from the austenitic phase, often called the parent phase, martensite starts to form at a temperature designated as MS and upon reaching the lower temperature, $M_F$, the alloy is completely martensitic. Upon heating from below the $M_F$ temperature, the martensite starts to revert to the austenitic structure at $A_S$, and when the temperature designated as $A_F$ is reached, the alloy is completely austenitic. These two phases or crystalline structures have very different mechanical properties: the Young's Modulus of austenite is ~$12 \times 10^6$ psi, while that for martensite is ~$4 \times 10^6$ psi; and the yield strength, which depends on the amount of cold work the alloy is given, ranges from 28 to 100 ksi for austenite and from 10 to 20 ksi for martensite.

The unique feature of shape memory alloys is their ability to recover deformation. When a shape memory alloy specimen, in its martensitic form is subjected to stress, the strain is accommodated by the growth and shrinkage of individual martensite variants rather than by the mechanisms which prevail in conventional alloys: slip, grain boundary sliding and dislocation motion. When deformed martensite is heated to the austenite finish temperature $A_F$, the part reverts to its original undeformed state. Thus, for medical implant uses, it is possible to develop a design where the device is stored below body temperature in its unformed shape, and upon insertion into the body, the temperature of the device raises to that of the body, at which point the device reverts to the austenitic structure. In the instant application, the fasteners may be optionally made of an SMA such as NiTi.

It is within the scope of the present invention that such fastening systems as herein described are able to be fastened into bodily tissue in less time than would be required to suture the device into place. In the instance described here (the placement of an access port for a gastric band), the placement and fixation of the fastening system should take no more than five minutes. Additionally, the fixation system is able to be entirely unfastened and removed from the tissue in order to facilitate repositioning of the device, or to remove the implanted device entirely. Such implantation and extraction will not cause increased trauma to the patient, and the fixation system will not cause more adhesions than the traditional suturing method. The average surgeon or other health professional is reliably and consistently able to perform fixation and extraction of the fastening system.

Additionally, during the manufacture of such fixation systems described herein, the size of the fasteners determines the depth into the bodily tissue into which the fasteners will deploy. In the instant case, fixation of an access port should occur at a depth below the device not to exceed 3 mm. Also, in such a use, the bodily tissue into which the fasteners are deployed is the fascia. However, it is within the scope of the invention that the bodily tissue to which the device is attached will vary depending on the specific device. Additionally, the attachment of the fastening system into tissue will not cause tissue damage during placement or during body motion; for example, an access port for a gastric band is often attached directly over the rectus abdominis. Further, the fixation of the device is of equivalent or greater strength to sutures and resists becoming dislodged or disconnected in order to accommodate a long-term implant.

The invention as described herein may be used with any type of implantable device. Examples of such would include internal monitors, ports, pacemakers, therapeutics, drug delivery systems, neurostimulators, orthopedic devices, tendon repair, etc. For ease of explanation, the invention will now be described as depicted in FIGS. 1-40, wherein the invention is shown used in conjunction with an access port. One of skill in the art will recognize that the present invention may be used with other types of implantable devices, and that the invention may take other forms analogous to those depicted herein.

Additionally, in the accompanying figures, the housing is shaped as a ring, and may accordingly be described as such. However, one of skill in the art will recognize that the shape of the housing is dependent on that of the device, such that the present invention is not limited to devices in which the housing would be circular.

FIG. 1 depicts an access port fastening system according to one embodiment of the present invention. The access port 10 includes a septum 11, which in practice is pierced by a needle to input fluid such as saline into the access port for use with, for example, a hydraulic operated gastric band.

Figure 3:
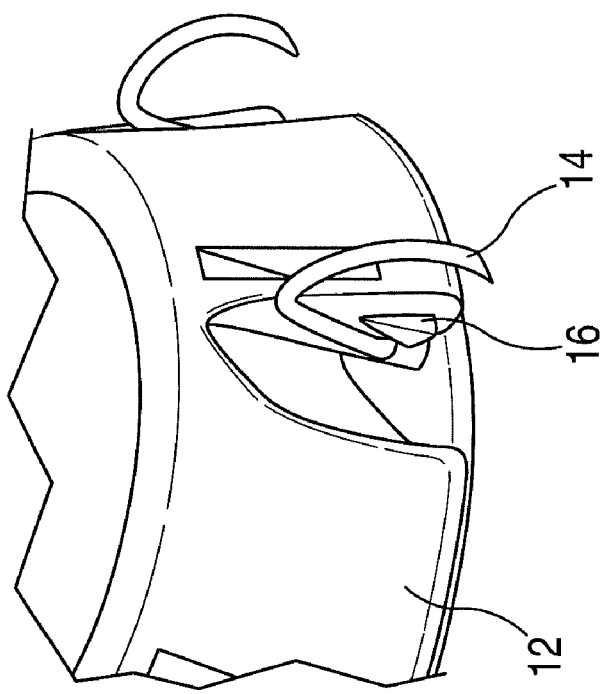
FIG. 3 is a detail elevation view of the radial pivot fastener of FIG. 1 with staples in pre-deployment position.

The access port 10 includes a detachable housing 12 which surrounds the outer perimeter of the access port. The detachable housing 12 may be in the form of a molded ring with a frusto-conical outer shape that snaps over an existing access port 10. The housing 12 includes notches or openings 15. The notches house fasteners 14. The notches or openings 15 may take any form necessary to adequately house the fastener 14 while allowing movement of the fastener 14. It is within the scope of the invention that at least three fasteners 14 be present in order to minimize the possibility of movement or dislodgement of the device. As shown in FIGS. 1-4, the fasteners 14 are attached to the ring 12 by a perpendicular segment engaged through a hole and are thereby pivotally connected to the ring 12. The fasteners 14 have a first or predeployed position as shown in FIGS. 1 and 3 and a second, deployed or secured position as shown in FIGS. 2 and 4. To move from the first to the second position, the fastener rotates about an axis of the fastener, and in the illustrated embodiment the fastener pivots in a radial plane. The notch 15 accommodates this rotation and a small locking tab 16 holds the fastener in position after rotation. In one embodiment, the fasteners 14 may be 2-legged staples. In another embodiment, the staples are rigid, such that they do not deform during the rotation into the fascia of a patient. For such applications conventional metals are suitable. Furthermore, the staples may be shaped as a "U" or variations thereof, including substantially shaped as:

When in the second, deployed position, the fastener 14 is held rigidly in place by a locking tab 16, and fastener 14 may flex to allow the fastener to pass into the locked position. The formation of the locking tab 16 may be such that upon movement of the fastener 14 from the first to the second position an audible click is heard by the surgeon to indicate that the fastener 14 is fully engaged by the locking tab 16. The click may also be tactile, allowing the surgeon to feel and confirm through the proximal handle that the fastener is fully engaged by locking tab 16. When in the second position an access port 10 is secured within the housing 12 in the patient by the fasteners 14 which interface with the fascia of the patient. Essentially, the fascia or other bodily tissue is secured between the fasteners 14 and the housing 12 or device 10. As seen in FIG. 2, tips of the fasteners 14 nest against a bottom surface of the access port 10, in effect sandwiching the port between the ring-shaped housing 12 and the fasteners. Furthermore, the housing 12 may contain pegs (not shown) which engage suture holes (not shown) which surround the perimeter of the device 10.

Figure 5:
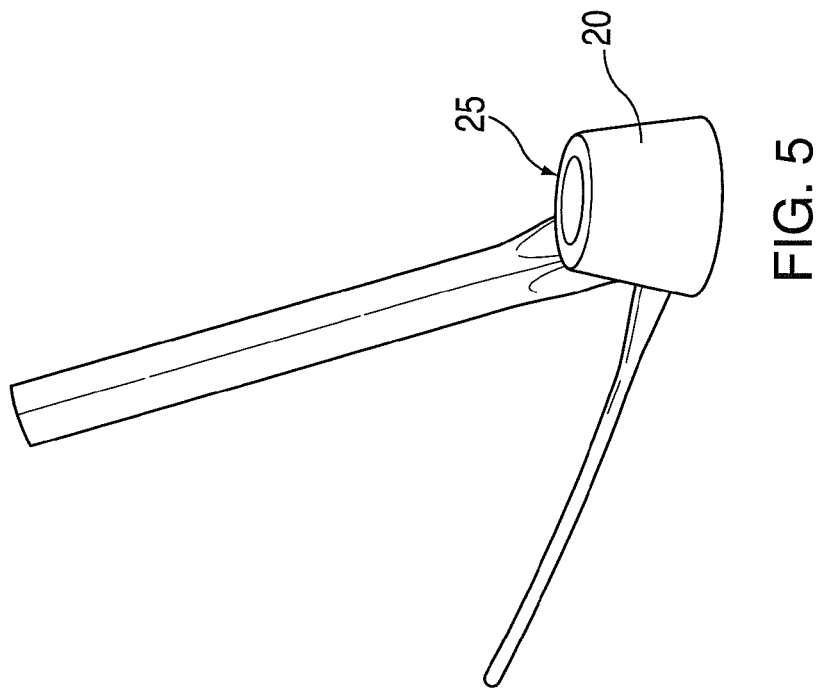
FIG. 5 is an elevation view of a delivery system.

FIGS. 5-8 depict the access port of FIG. 1 and its interaction with an access port delivery system 20. As shown in FIG. 5, the access port delivery system 20 may have a finger depression 25 on the distal end of a port cover 21 which is used by the operator to help hold the access port and the delivery system in place at the delivery location, stable and properly aligned. The finger depression 25 allows for tactile positioning and finger pressure can be applied to the top of the port cover distal end to increase placement confidence.

Figure 6:
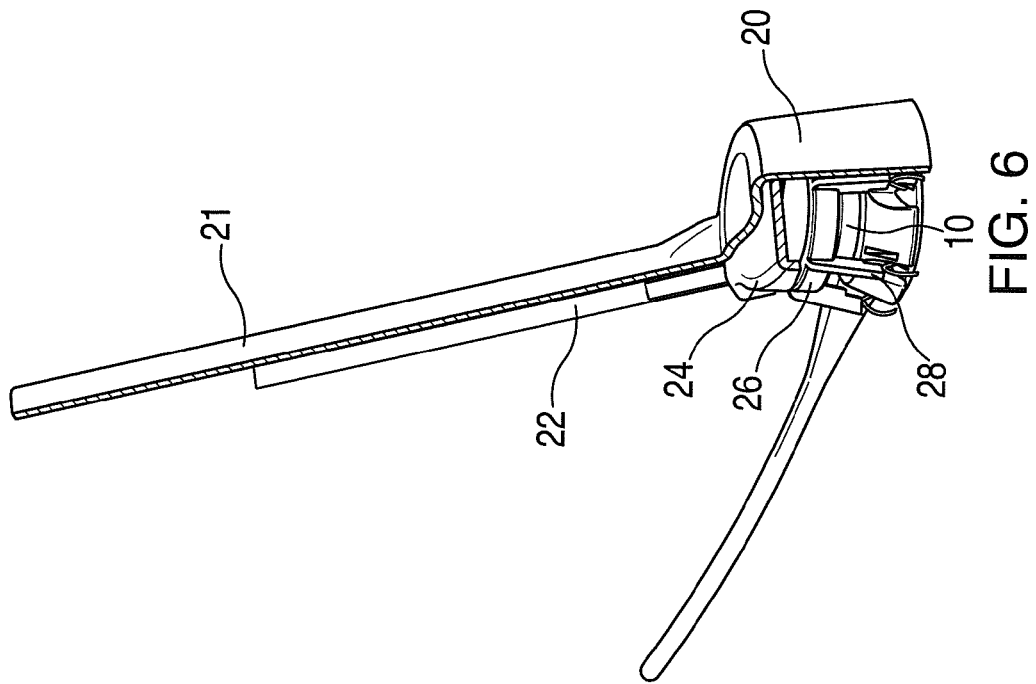
FIG. 6 is a cutaway view of the delivery system shown in FIG. 5 and a port fastener.

The delivery system 20 comprises a port cover 21 with a distal end having an open bottom that descends down over and captures the access port 10, and a proximal portion that extends upward at an angle therefrom toward a handle. The port cover 21 houses a rod-like plunger 22, a slide pusher 24, and a slide assembly 26, as seen in FIG. 6. The port cover may be formed in any shape necessary to substantially cover the access port 10, and in the illustrated embodiment has a frusto-conical distal end that conforms over the housing 12. The delivery system 20 interacts with a number of different proximal handle configurations, such as shown in FIGS. 9-19.

Figure 7:
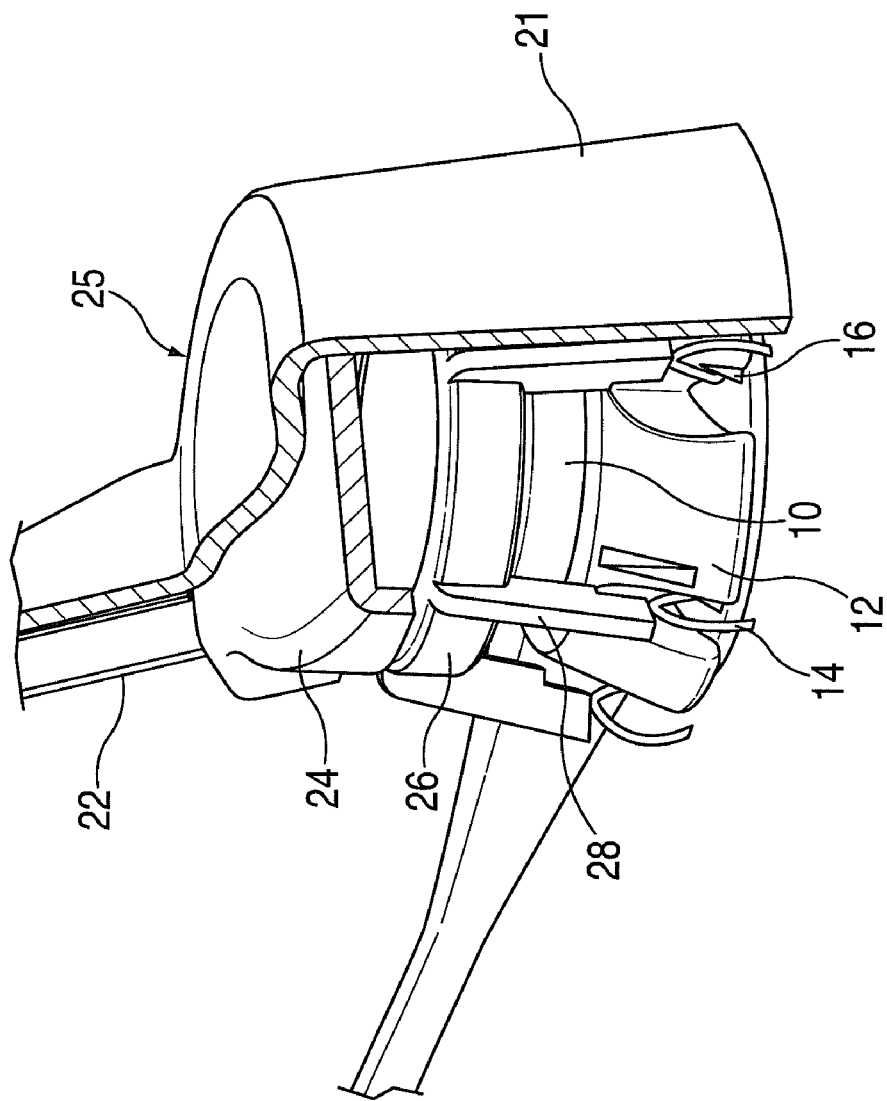
FIG. 7 is a detail cutaway elevation view of the distal end of the delivery system of FIG. 6 and a port fastener in pre-deployment position.
Figure 15:
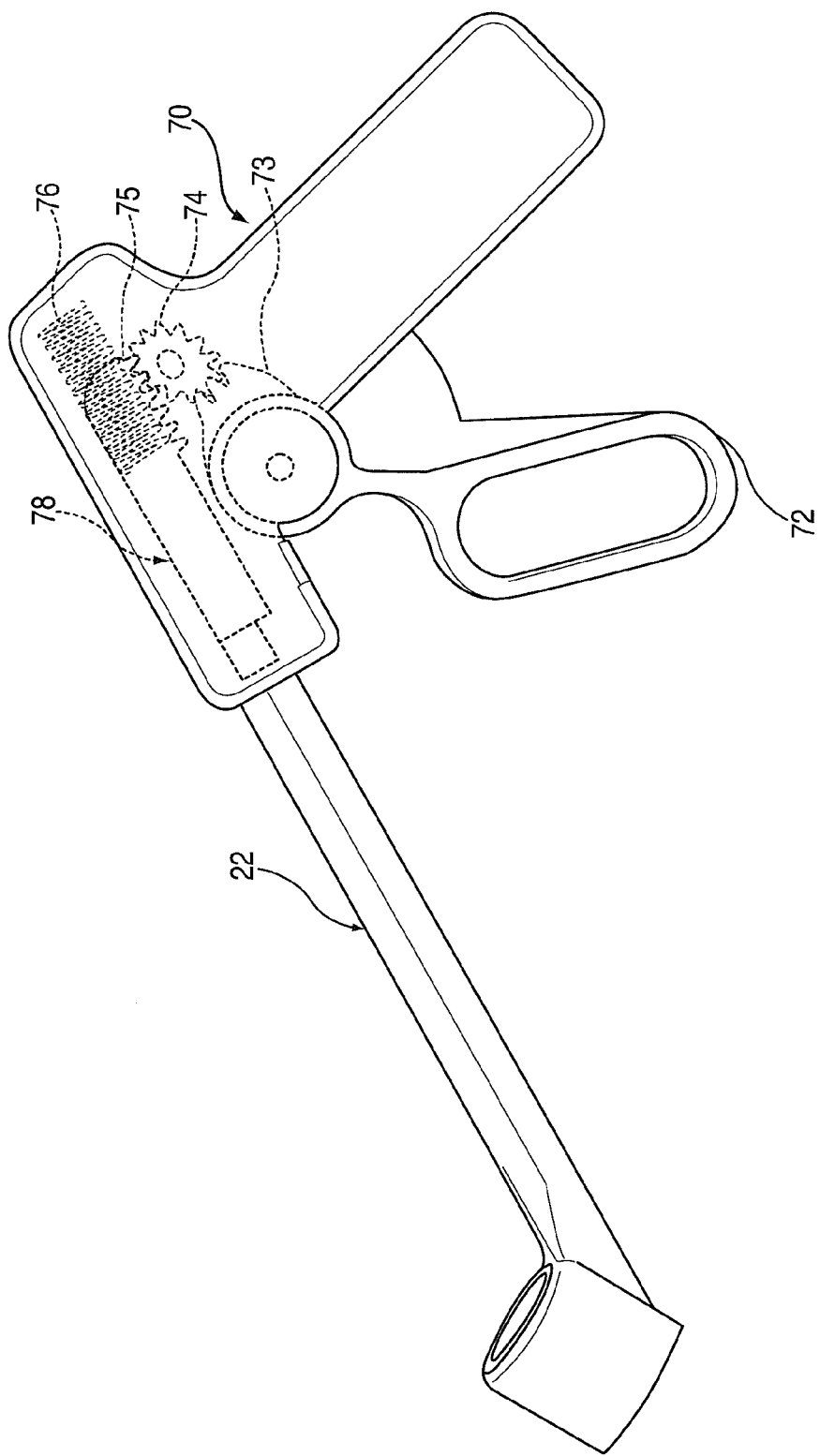
FIG. 15 is an elevation view of another pistol grip handle configuration for a delivery system.
Figure 16:
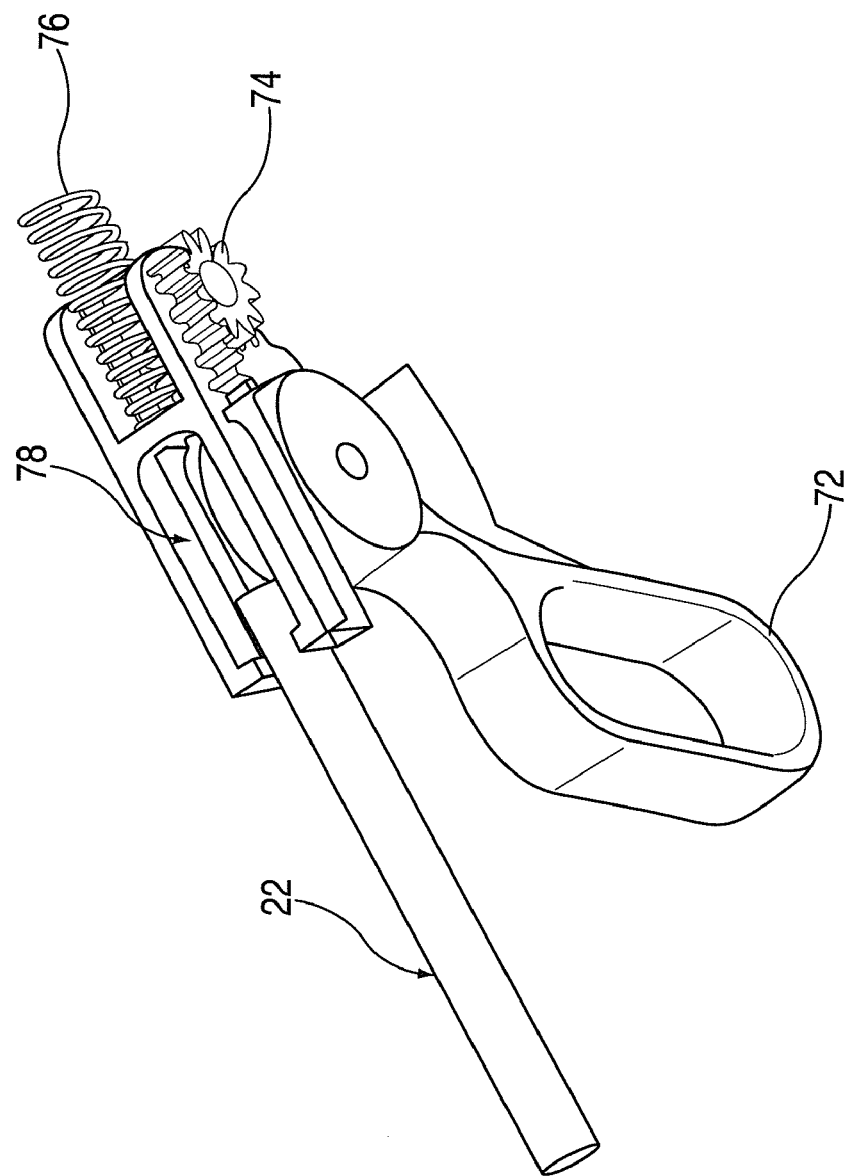
FIG. 16 is a detail view of the gear train mechanism of the delivery system of FIG. 15.

The plunger 22 provides the operative means for the delivery system 20 and is connected to a firing means which will be described below. Upon actuation of the firing means the plunger 22 moves in the direction of the access port 10 which, as illustrated in FIG. 6, is downward at an angle to the vertical. This movement causes the slide pusher 24 to be actuated. The slide pusher 24 transfers the energy of the moving plunger 22 to the slide assembly 26. The slide pusher 24 is wedge-shaped as seen best in FIG. 7 so as to cam and deliver downward force to the slide assembly 26 as it slides across the top surface thereof. The slide assembly 26 has a substantially round shape and encircles the access port 10. As seen in FIG. 7, a series of elongated beams 28 spaced around the periphery of the slide assembly 26 extend downward into the notches 15 in the housing 12 and contact the fasteners 14 therein. In other applications, the slide assembly may take a form suitable to the device and housing to be implanted. Upon actuation, the slide assembly 26 is forced in the direction of the access port 10. Alignment tabs 30 as seen from below in FIG. 8 assist the alignment of the slide assembly 26. The alignment tabs 30 are attached to the port cover 21 and interact with the access port 10 to ensure proper alignment. The movement of the slide assembly 26 causes beams 28 attached to the slide assembly 26 to act upon the fasteners 14. The imparting of force on the fasteners 14 allows them to rotate in the ring holes (not shown) and to transcribe an arc defined substantially by the notch 15. This rotation coincides with a movement from the first to the second position discussed above. As the beams 28 continue to be moved towards the access port 10, the fasteners 14 are forced past the locking tabs 16 into tissue below the access port 10 to reach the second position, and are held in place by the locking tabs 16. In this position, with the fasteners 14 deployed as seen in FIG. 8, the access port 10 is rigidly held in place by the fasteners 14 and their interaction with the fascia or other tissue of the patient. At this stage the port cover 21 may be retracted upward from around the access port 10. A feature on the port cover 21 captures the access port 10 therein until deployment is complete, at which time the port is released.

FIG. 9 shows an access port delivery system complete with a firing means 40 in a pencil-grip style handle attached to the proximal end of the upwardly angled shaft of the delivery system 20, which is shown at 60° from the horizontal. FIG. 10 shows a cross sectional view of the firing means 40 in the starting or loaded position. In this position, the spring 42 is compressed, and a latch 44 that is connected to a rod 46 on the proximal end of the plunger 22 is secured by a rib 48 to prevent the compressed spring 42 from expanding. The firing means has a button or trigger 50 connected to a lever 52. As shown in FIG. 10 the spring 42 and rod 46 are in a housing 54.

As shown in the fired position of FIG. 11, upon application of a predetermined force to the trigger 50, the lever 52 acts on the housing 54. The housing 54 pivots on a fulcrum (not shown), this pivoting action lifts the latch 44 above the end of the rib 48, thus dislodging the rod 46 and allowing it to advance distally. Upon lifting, the spring force of the compressed spring 42 drives the plunger 22 in the direction of the access port and actuates the mechanism therearound as discussed above. In such a configuration the plunger travel, speed and impact force can be determined to meet the application needs. As tested, the plunger travel was between 0.25 and 0.75 in, and can develop up to 50 lb. of force on the plunger, depending upon the spring used in the application. Deployment of the plunger 22 is thus instantaneous with a high impact speed, though a slower deployment mechanism controlled by the surgeon may be provided.

An alternative handle configuration to the spring driven mechanism described above is shown in FIG. 12. FIG. 12 shows a palm grip actuated firing mechanism 60. The palm grip is a very simple lever design requiring only a single moving part to move the plunger 22. In a first or starting position as shown in FIG. 13, there is a moving handle 61 (or lever), a stationary handle 62 (or housing), a pivot point 64, and an actuating tip 66. The handle is oriented generally horizontally and attaches to the upwardly-angled shaft of the delivery system 20, which is shown at 60° from the horizontal.

In operation the user squeezes on the moving handle 61 forcing it in the direction of the stationary handle 62 to the fired position of FIG. 14. This movement forces the actuating tip 66 which is connectively engaged with the moving handle 61 and the pivot point 64 in a direction opposite the direction of movement of the movable handle 61. Through the use of the simple lever action, a comparatively small force applied to the moving handle 61 (lever) is amplified through the pivot point 64 and applied by the actuating tip 66 to the rod-like plunger 22. The plunger 22 is moved downward at an angle by the actuating tip 66 in the direction of the access port 10 and actuates the mechanism therearound as discussed above. The force produced by the palm grip actuated device is limited only by the strength of the user, as tested the device was capable of producing in excess of 50 lb. of force with a plunger travel of 0.25 in. Deployment speed is controlled by the operator. Alternatively, a geared mechanism could be produced that could produce equal or greater force although require a greater travel distance for the moving handle 61. The force produced by the device shown in FIGS. 12-14 could also be altered as necessary by moving the pivot point 64 nearer the plunger 22 to produce more force, or away from the pivot point to produce less force.

Yet another alternative firing means/handle configuration is shown in FIGS. 15-19. The pistol grip firing means 70 includes a trigger 72 having geared teeth 73 located on one end, a gear 74 which meshes with the geared teeth 73, a rack 75 driven by the gear 74, and a spring 76. The rack may also include a means 78 for gripping the plunger 22, which is slip fit within the delivery system 20 shaft.

Figure 17:
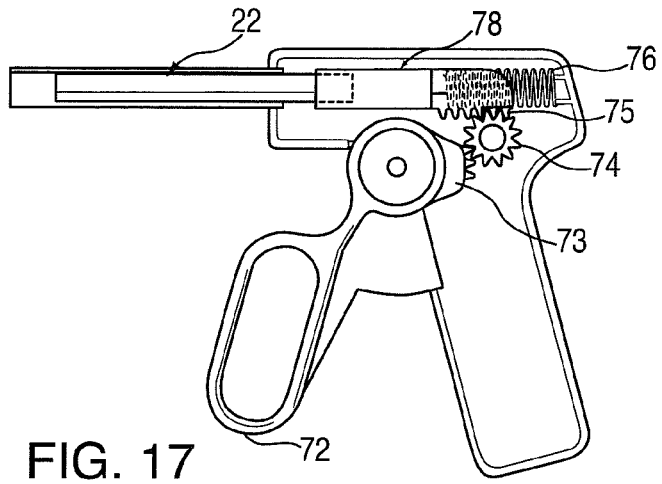
FIG. 17 is a detail cutaway elevation view of the delivery system of FIG. 15 shown in a starting position.
Figure 18:
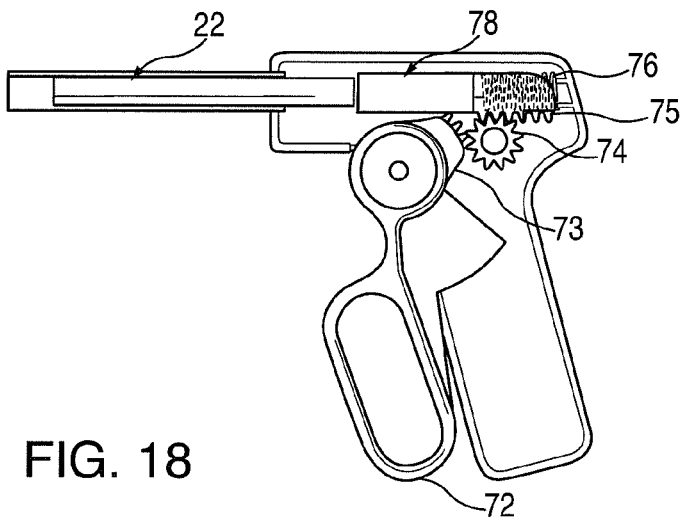
FIG. 18 is a detail cutaway elevation view of the delivery system of FIG. 15 shown in a full spring recoil position.
Figure 19:
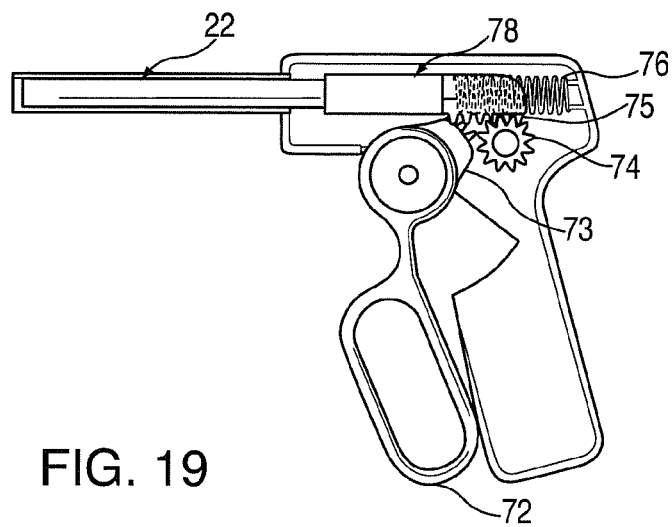
FIG. 19 is a detail cutaway elevation view of the delivery system of FIG. 15 shown in a fired position.
Figure 21:
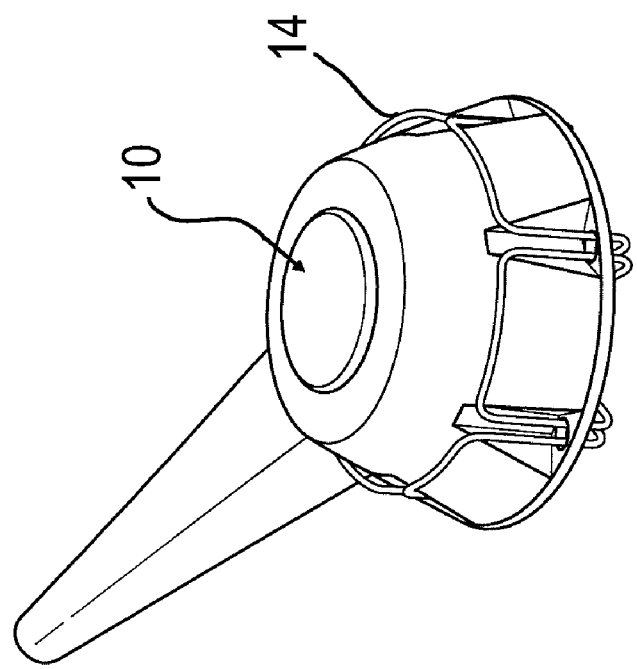
FIG. 21 is an elevation view of the continuous NiTi wire form fastener of FIG. 20 in post-deployment position.

The operative progression is shown in FIGS. 17-19. In the starting position of FIG. 17, the trigger is extended and the spring is under little or no tension. The geared teeth 73 are meshed with corresponding teeth of the gear 74 and with teeth on the rack 75. The plunger 22 is in the extended position. When the trigger 72 is depressed, the geared teeth 73 actuate the gear 74 and in turn cause the rack 75 to compress the spring 76 into the full spring recoil position, as shown in FIG. 18. At a predetermined distance the geared teeth 73 no longer engage the gear 74. At this point the gear 74 is free to spin. The stored energy in the spring 76 forces the rack 75 to move toward the plunger 22. The free spinning gear 74 allows the rack 75 to move, which in turn forces the rod-like plunger towards the access port 10 and actuates the mechanism therearound as discussed above, and as seen in the fired position of FIG. 19.

Another feature which may be incorporated into the pistol grip firing means 70 is a lock (not shown), which after the spring 76 is compressed prevents the gear 74 from spinning. Then when desired the operator can release the lock, thereby allowing the spring 76 to expand as discussed above.

As tested, the pistol grip firing means 70 permits the plunger to travel approximately 0.4 in and can produce in excess of 50 lb. of force. One distinct advantage of this embodiment over, for example, the movable grip device discussed above is the instantaneous deployment having a very high impact speed.

Figure 20:
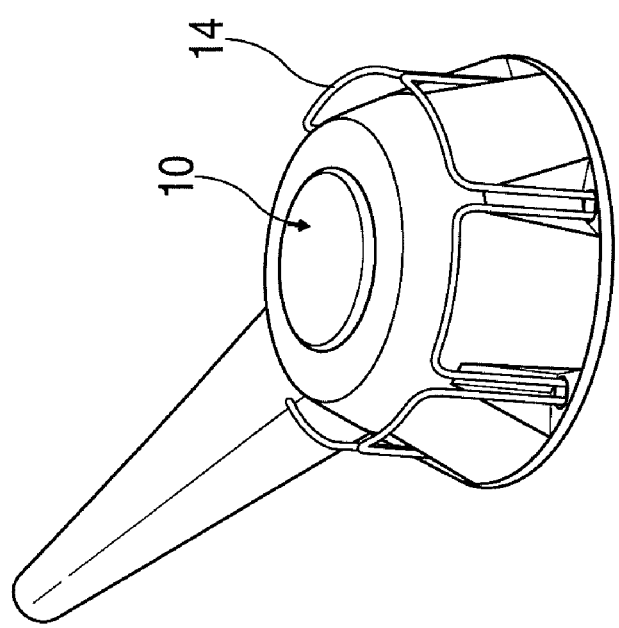
FIG. 20 is an elevation view of a continuous NiTi wire form fastener in pre-deployment position.

In FIG. 20 a further embodiment of the present invention is shown. The use of NiTi (Nitinol) or SMA alloy materials is well known in the medical arts as discussed above. As shown in FIG. 20 NiTi fasteners are shown in a pre-deployment state. The fasteners 14 are arranged in a continuous wireform with legs attached to the access port 10 through holes therein. In operation the fasteners 14 are depressed into the fascia of the patient to secure the access port. The NiTi fasteners 14 have the unique ability to change their shape when heated, e.g. to body temperature. As shown in a post-deployment state in FIG. 21, when the fasteners are deployed they can change shape to bend under and towards the center of the access port 10 and secure it in place.

Figure 22:
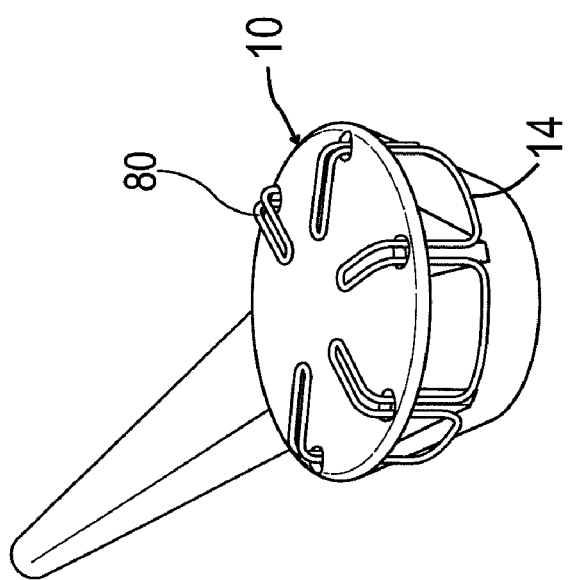
FIG. 22 is a bottom elevation view of a straight leg, blunt tip continuous wire form fastener.
Figure 23:
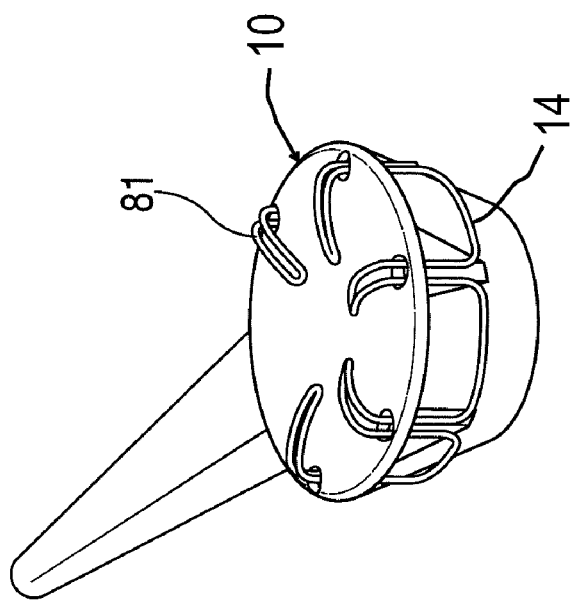
FIG. 23 is a bottom elevation view of a curved leg, blunt tip continuous wire form fastener.

In FIG. 22 the fasteners 14 are shown with straight legs 80 parallel to a base of the access port 10 in a deployed state. Alternative configurations include curved legs 81 as shown in FIG. 23. By virtue of the continuous wireform, the fasteners/legs are formed by narrow closed-loop projections with blunt tips. Using the curved legs 81 which track into the base of the access port 10, the fascia can be pinched between the fastener and the underside of the access port. A further alternative is shown in FIG. 24 where the tips of the continuous wireform fastener legs 81 are coated with a molded tip 82. The molded tip may be formed in a shape that will assist in piercing the fascia of the patient. This eliminates the need to form the fastener 14 into a shape for piercing. Additionally, the tips 82 may be formed of a bio-absorbable material.

Figure 26:
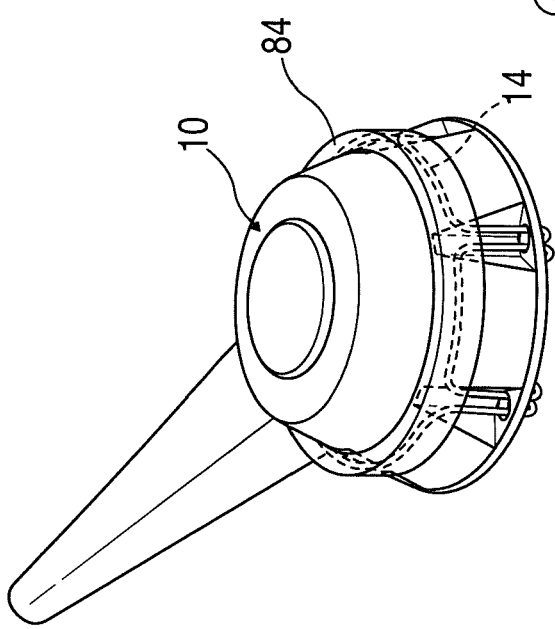
FIG. 26 is an elevation view of a continuous NiTi wire form fastener with ground tips in post-deployment internal position.
Figure 27:
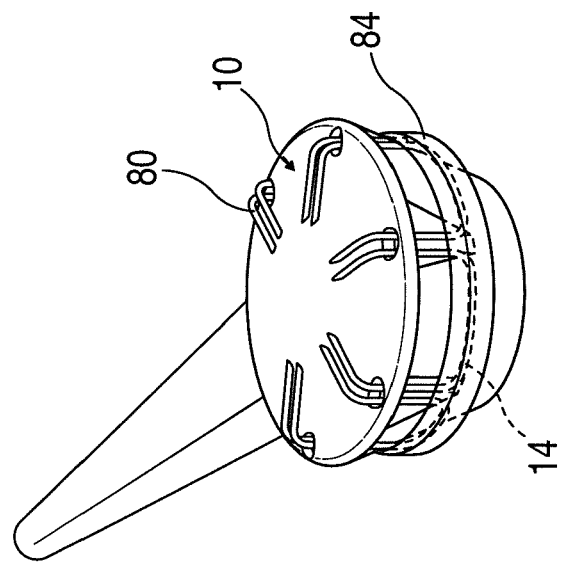
FIG. 27 is a bottom elevation view of the continuous NiTi wire form fastener with ground tips of FIG. 26 in post-deployment internal position.
Figure 25:
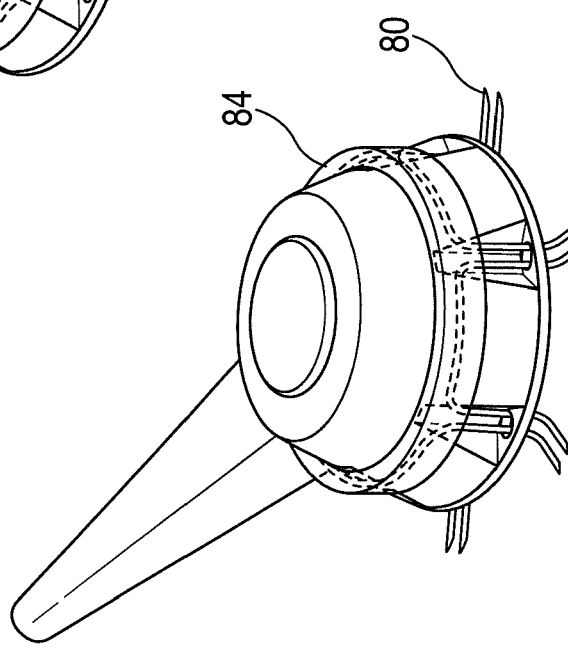
FIG. 25 is an elevation view of a continuous NiTi wire form fastener with ground tips in post-deployment external position.

In another embodiment of the present invention, the NiTi fastener can be continuously formed as one-piece along with an insert-molded ring 84, as in FIGS. 25-27. The use of the ring 84 allows for the NiTi fasteners 14 to be formed with a continuous one-piece construction. After the insert-molded ring 84 with the fasteners 14 is formed, the ends of the legs 80 can be ground off to produce individual substantially U-shaped fasteners 14. The ring 84 insures that the fasteners 14 can be inserted as a unit as discussed above, and the grinding of the legs ensures a sufficiently sharp point to more easily pierce the fascia. As shown in FIGS. 25 and 27, the legs can be formed and positioned in the ring 84 so that after bending due to heating, the legs 80 face internally to the access port 10 or externally to the access port 10.

Figure 29:
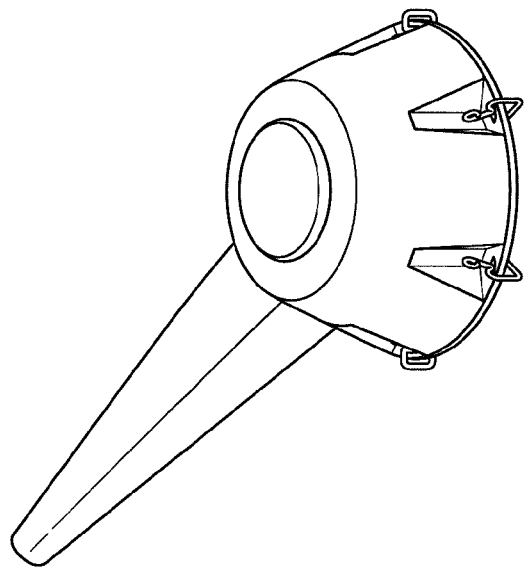
FIG. 29 is an elevation view of the radial slide fastener of FIG. 28.
Figure 30:
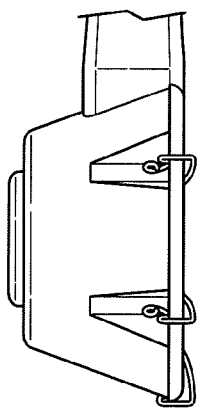
FIG. 30 is an elevation view of a radial slide fastener with curved legs.
Figure 28:
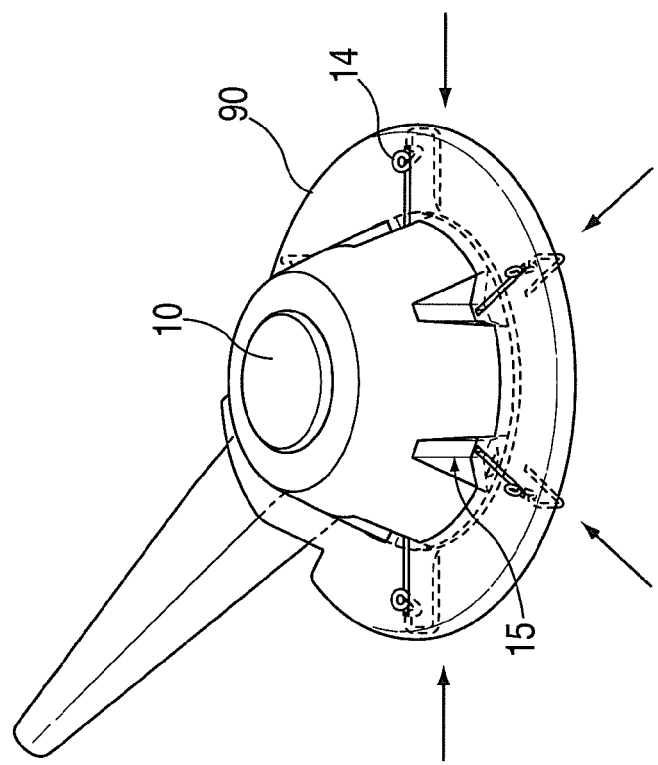
FIG. 28 is an elevation view of a radial slide fastener with straight legs and a staple guide.

Yet another embodiment of the present invention is a two-part radial slide fastening system as shown in FIGS. 28-34. FIG. 28 shows a guide 90 formed with a plurality of individual fasteners 14. The guide 90 may be a molded circular flange-like member as shown. The fasteners 14 are slidable in the guide 90 from a first to a radially inward second position. In operation the guide 90 is placed over the access port 10 and aligned with notches 15. The fasteners 14 are formed of a spring like material and shaped to attach to the access port 10. The fasteners 14 are slid from a first position as shown in FIG. 28 to a second position as shown in FIG. 29. Small protrusions on each fastener 14 may snap into place in suture holes of the access port 10, as seen in FIG. 29. The fasteners 14 pierce the fascia and securely hold the access port 14 thereto. As previously described, the fasteners may have straight or curved legs, the former shown in FIGS. 28 and 29 and the latter in FIG. 30. After the sliding of all of the fasteners from the guide 90 onto the access port 10, the guide may be removed if it is not part of the final implanted device. Alternatively, the guide 90 may also be a permanent part of the implantable device.

Figure 32:
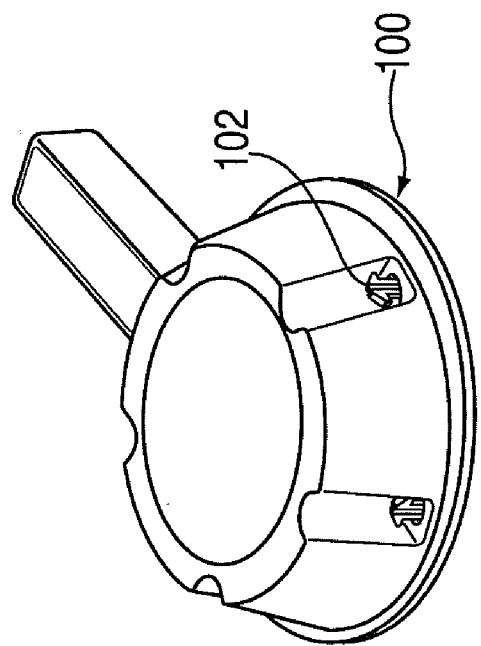
FIG. 32 is an elevation view of the two-part fastening system of FIG. 31 after installation.
Figure 31:
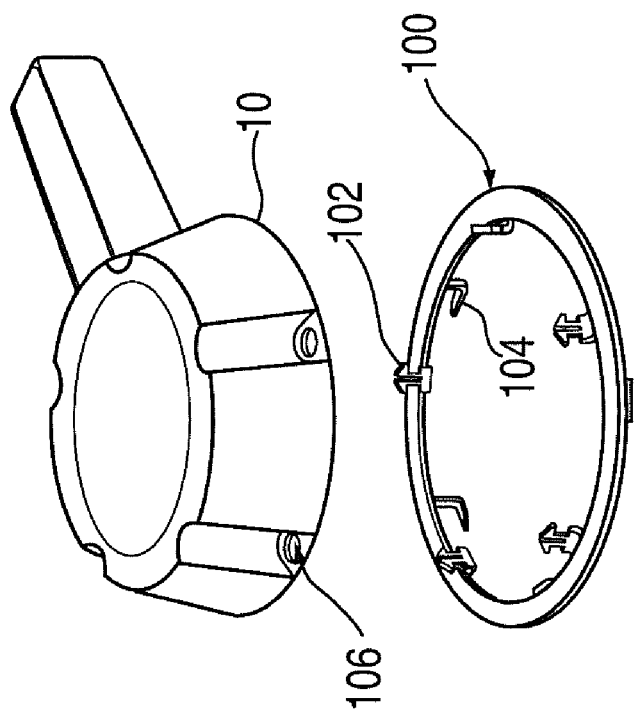
FIG. 31 is an elevation view of a two-part fastening system before installation.

A further two-part fastening device includes a pre-formed ring 100 (FIG. 31 and FIG. 32). The ring includes a first securing means 104 for attaching the ring 100 to the fascia. The ring also includes a second securing means 102 for attaching an access port 10 to a secured ring 100. In operation, the ring 100 is placed upon the fascia and then twisted to engage the fascia in the first securing means 104. The access port 10 is then placed upon the ring 100 and engages the second securing means 102 via holes 106 in the access port. This design allows for positive attachment and re-installation repeatability without disengaging the pre-formed ring.

Figure 34:
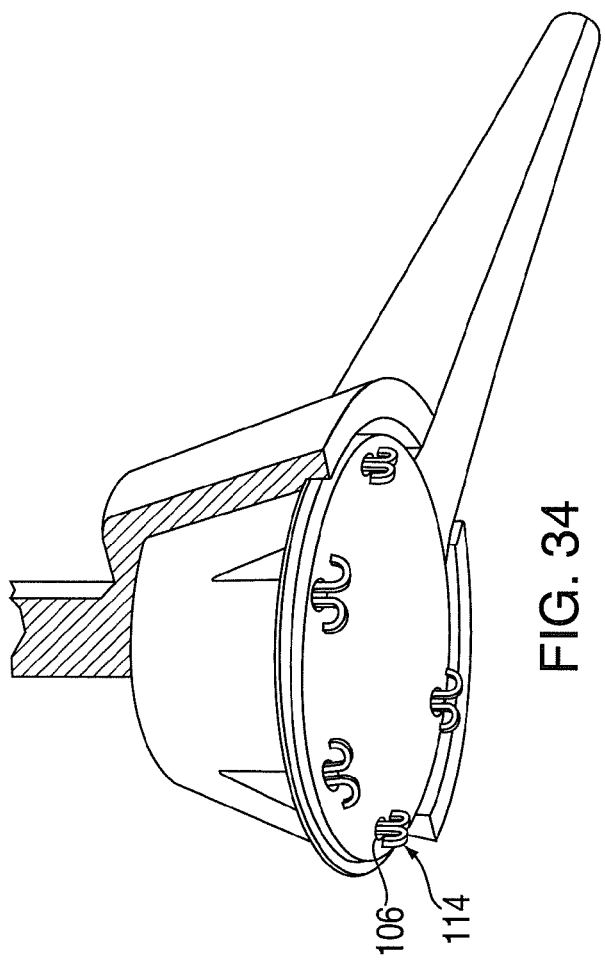
FIG. 34 is an elevation view of the two-part fastening system of FIG. 33 after installation.
Figure 33:
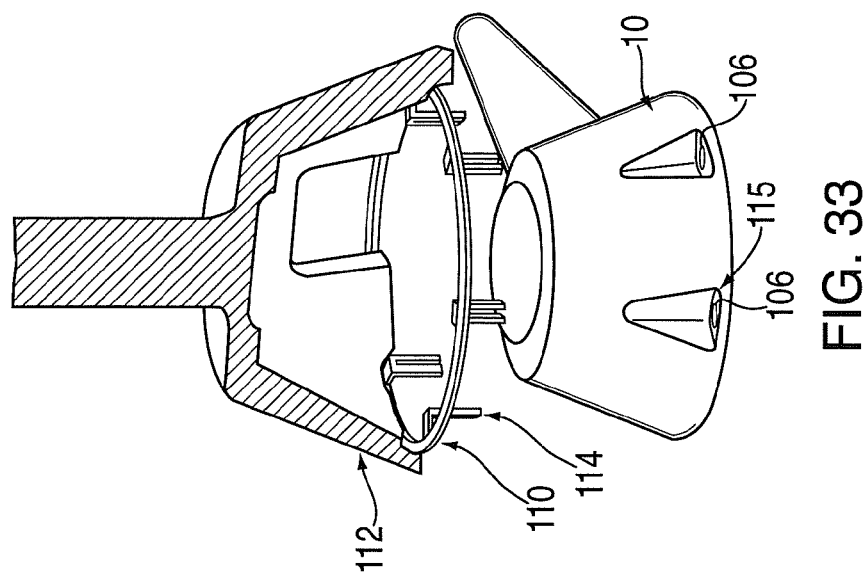
FIG. 33 is an elevation view of another two-part fastening system before installation.

FIG. 33 and FIG. 34 depict pre- and post-installation stages, respectively, for yet another two-part fastening device comprising an applicator 112 and a ring 110 having NiTi fasteners 114. In practice, the ring 110 is inserted into the applicator 112. The applicator 112 is placed over the access port 10 with the fasteners 114 aligned with notches 115 and holes 106. The fasteners 114 are forced through the holes 106 and engage the fascia of the patient upon which the access port 10 rests. Through the heating process, the fasteners 114 change shape and secure the access port to the fascia. After a predetermined time, the applicator can be removed.

Figure 35:
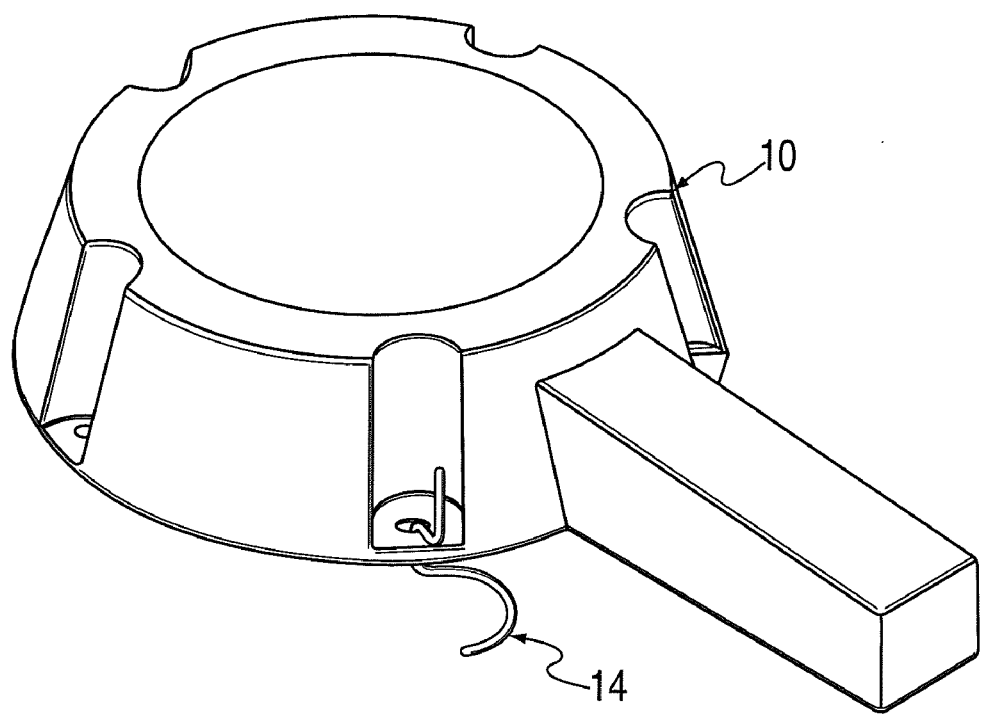
FIG. 35 is an elevation view of a stand-alone fastener incorporated into a device.
Figure 36:
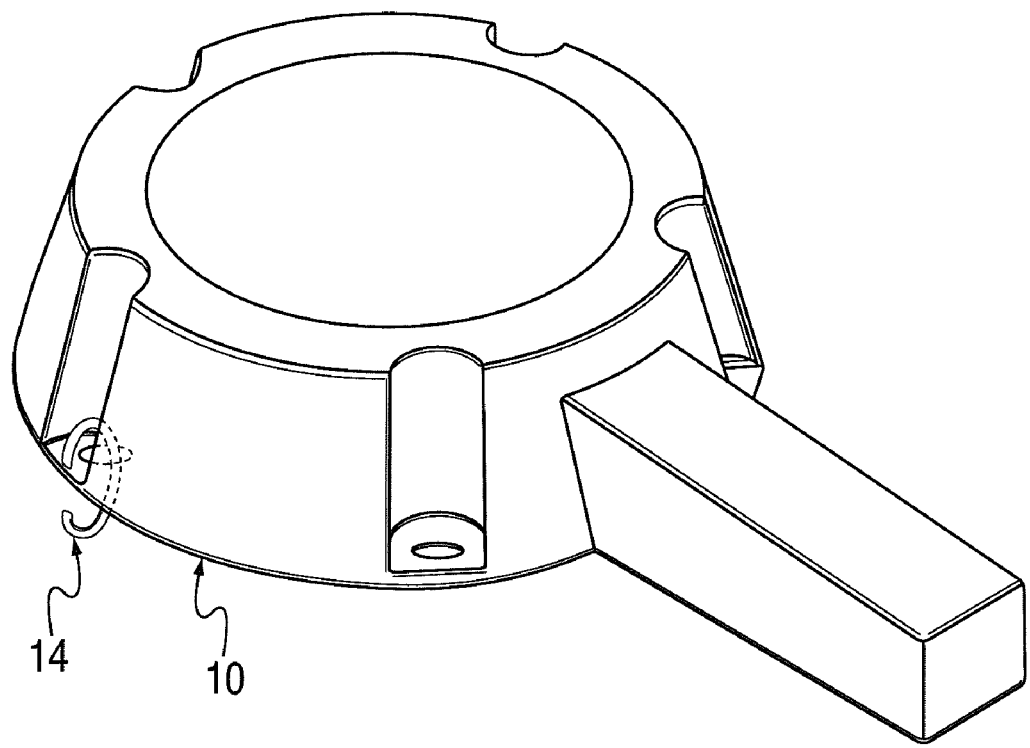
FIG. 36 is an elevation view of another stand-alone fastener incorporated into a device.
Figure 37:
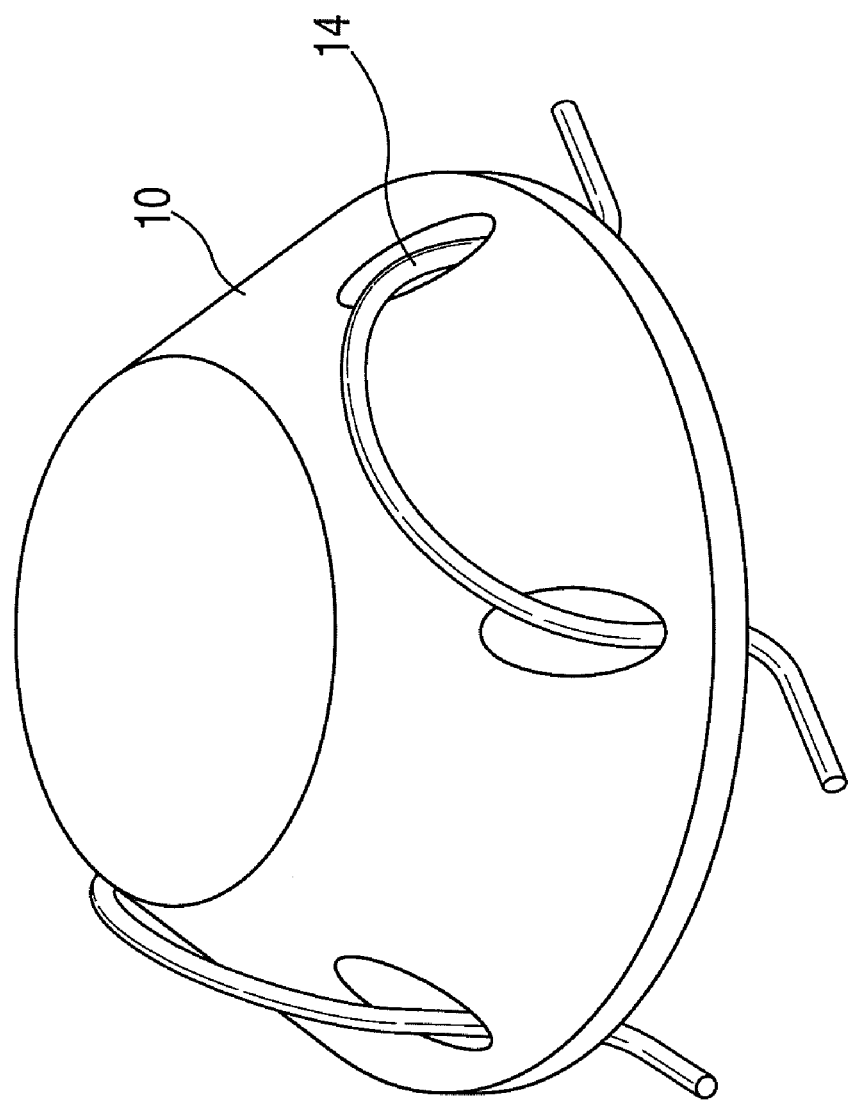
FIG. 37 is an elevation view of another stand-alone fastener incorporated into a device.
Figure 38:
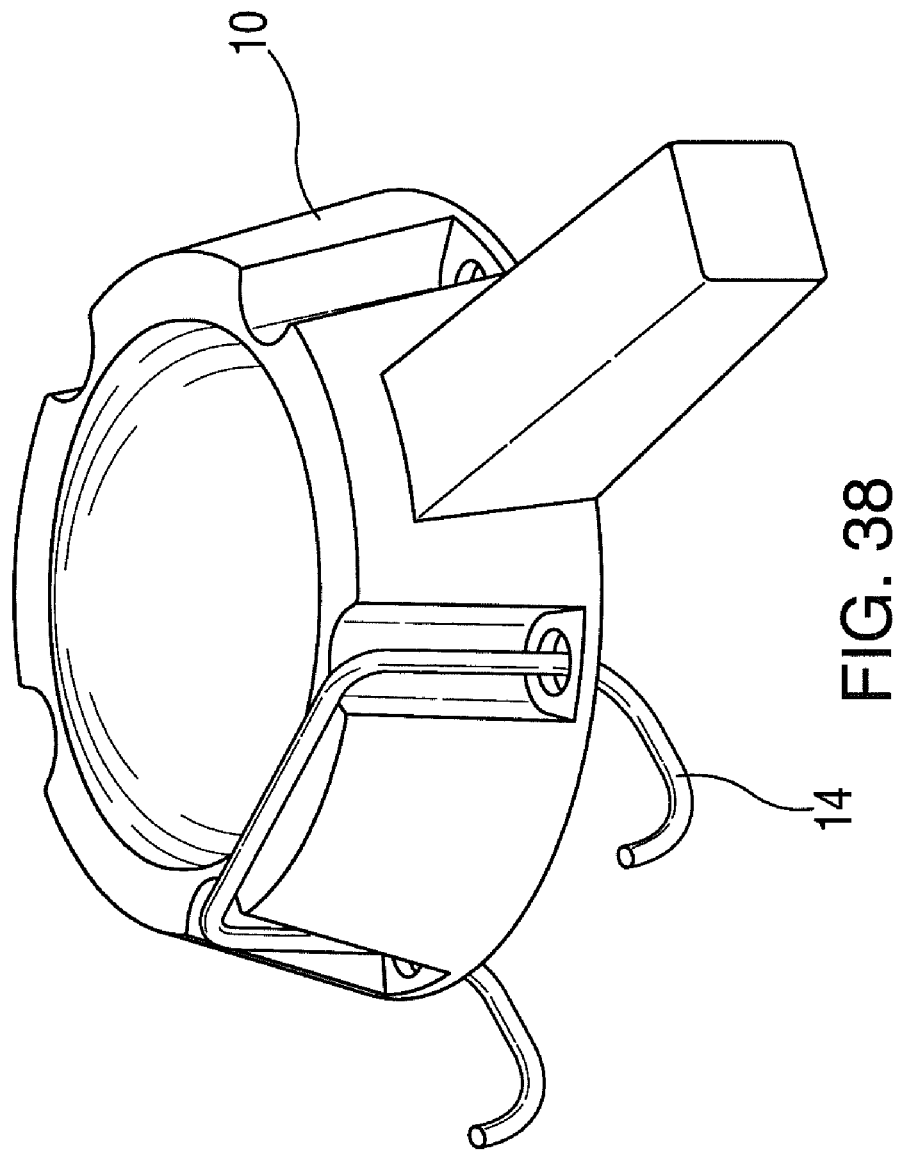
FIG. 38 is an elevation view of another stand-alone fastener incorporated into a device.

Another embodiment of the present invention regards stand alone fasteners. As shown in FIGS. 35-38, a variety of designs can be used to secure an access port 10 to the fascia of a patient. The fasteners may incorporate NiTi so that the fasteners change shape upon application of a predetermined amount of heat. These fasteners 14 may be inserted singularly, or as part of a pre-formed ring as discussed above. When inserted singularly, the fasteners 14 may be straight rods or may have some pre-formed shape which may be heightened through the heating process. In FIG. 35, the fastener 14 takes on a curly, pig-tail shape. In FIG. 36 the fastener takes on a substantially C-shaped appearance. FIGS. 37 and 38 use U-shaped fasteners 14, the ends of which bend, linearly when heated to form an omega shape as shown in FIG. 37, or perpendicularly to the shape as shown in FIG. 38. These shapes can be chosen as desired for a specific application.

Figure 40:
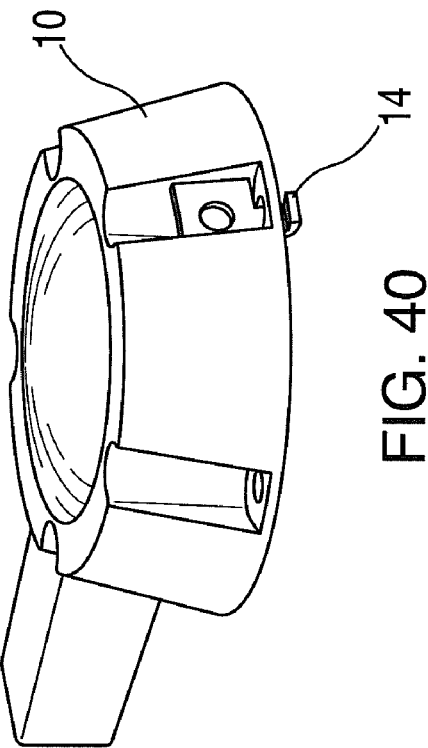
FIG. 40 is an elevation view of the stand-alone fastener of FIG. 39 in a post-installation position.
Figure 39:
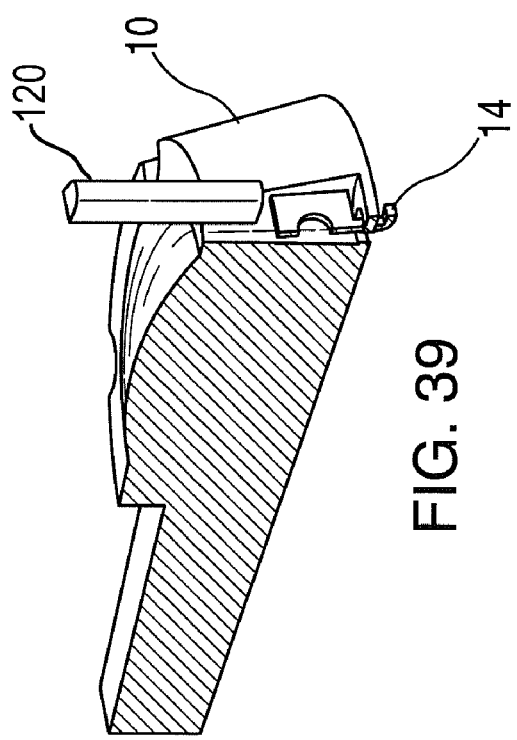
FIG. 39 is an elevation view of another stand-alone fastener incorporated into an injection port in a pre-installation position.

Yet another embodiment of the present invention is shown in FIG. 39. In FIG. 39 the fasteners 14 are slidably installed in the access port 10. This may be accomplished by cold molding of the NiTi fastening system into the device, and allows positive attachment and repeatable re-positioning. Through the use of an installation tool 120, the fasteners are forced through holes in the bottom of the access port 10 and engage the fascia. By installing the fasteners as an integral part of the access port 10, no ring or housing is needed as discussed above for housing the fasteners. The installation tool 120 could be part of a triggering device as disclosed herein. FIG. 39 is a pre-installation stage and FIG. 40 shows the fastener 14 in the engaged position.

As described above and shown in FIGS. 1-8, radial pivot fasteners are a simple delivery system, with direct drive. The associated delivery system actuates the pivot for radial entry. The staple may be stainless steel, titanium, Nitinol or Elgiloy™, or other suitable materials including other metals or plastics. The molded pivot/lock-out system may be designed to snap into the existing suture holes on implantable devices. Additionally, the simple staple shape allows for easy manufacturability. Such a system is self-puncturing, i.e. no pre-puncturing of the bodily tissue, e.g. fascia, is necessary. The curved nature of the staple allows the penetration into the bodily tissue as the staple advances to be predictable; and the pivoting nature of the curved staple generates an easy path through the tissue. Removal of the fastening system requires an extraction tool, and the staples will rotate out of the original entry path with only small resistance from ingrown surrounding tissue. However, the force required to remove the system is adequate to allow the staples to remain locked in position except during a removal procedure.

Continuous wire forms of the fastener system contemplated herein include blunt tips, molded tips, and ground or chopped tips. Blunt tip continuous wire systems, as shown in FIGS. 20-23 may require pre-puncture for insertion of the blunt tipped wire. The fastener assembly may be manufactured to require the locking feature to retain either the wire form or the overmolded ring. The simple wire form may be made of stainless steel, titanium, Elgiloy™, NiTi or other suitable materials. Removal of the fastener assembly may be done easily due to the blunt ends, which provide minimal tissue damage and trauma. Additionally, the blunt tip reduces the force necessary to remove the assembly. The continuous wire form assembly with molded tips, shown in FIGS. 20 and 24, does not require pre-puncture of the bodily tissue, and these tips allow for easy entry into the bodily tissue. Further, the chopped or ground blunt end continuous wire form assembly, FIGS. 25-27, also requires no pre-puncture of the bodily tissue, which also allows for easy entry into the tissue.

The radial slide fastener assembly, depicted herein with flat fasteners (FIGS. 28 and 29) and curved fasteners (FIG. 30), requires a larger entry site than the other fastener assemblies. The fasteners create a path through the bodily tissue that is simple and secure, with added retention in systems utilizing the curved fasteners. Removal of the systems is accomplished with an associated extraction tool that withdraws each fastener from their center position. Alternatively, the fasteners may be manufactured such that removal may be accomplished by lifting the assembly upwards, at which time the fasteners bend to a straightened position, allowing for easy removal.

Figure 41:
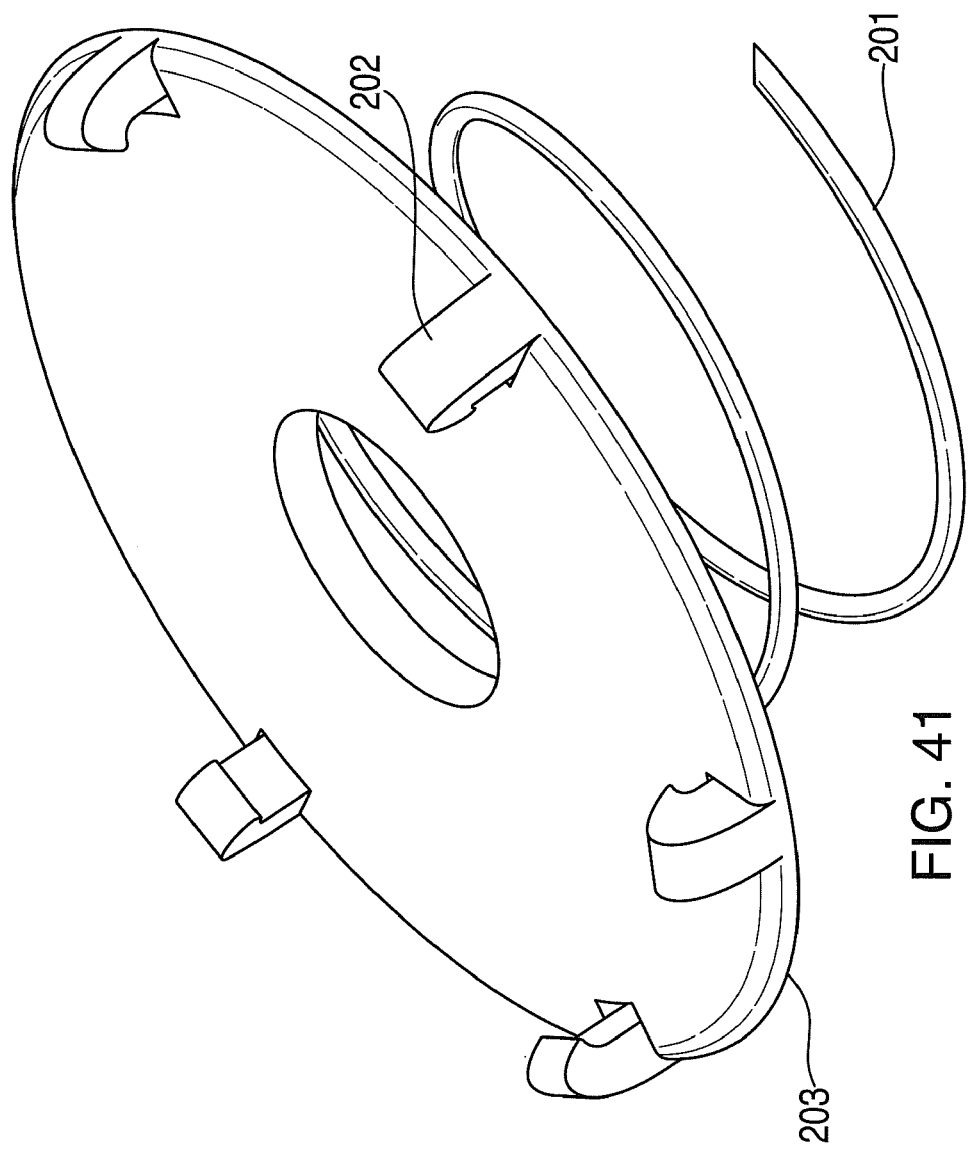
FIG. 41 is an elevation view of a helical coil fastener.

FIG. 41 depicts a helical coil fastener 201, which may optionally be utilized with a port that features a tubing connector extending from the center of the base. The corkscrew-type design is mounted to a separate disc 203 which snaps to the port at tabs 202, or alternatively, may be mounted to the port itself, centered on the base plate. The disc or port is manually affixed to the tissue by rotation of the disc or port, which causes the coil to travel on a helical path through the tissue. In one embodiment, the coil can have a sharpened tip.

Figure 42:
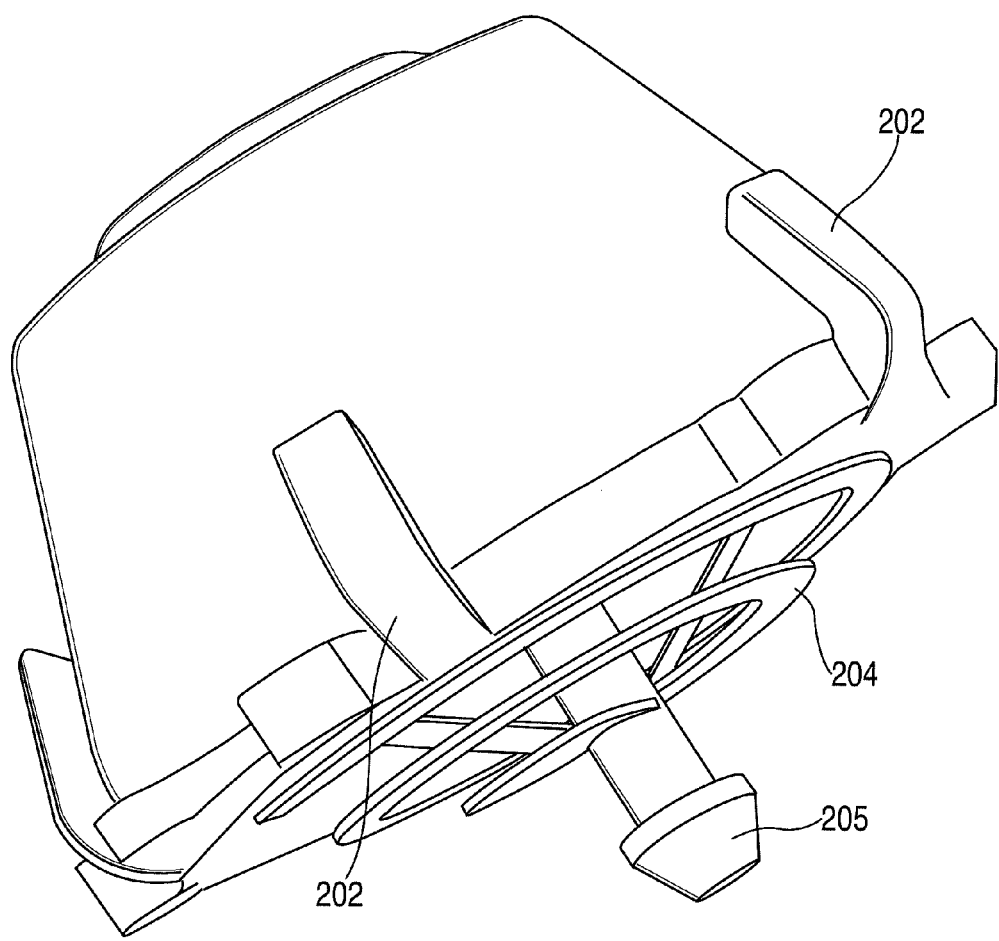
FIG. 42 is an elevation view of another helical coil fastener.
Figure 46:
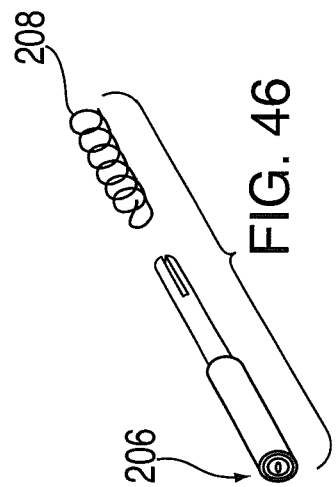
FIG. 46 is an elevation view of a driver tool of a fastening system for the horizontal coil fastening system of FIG. 43.

A variation of the helical coil fastener is depicted in FIG. 42. FIG. 42 depicts a flat spiral spring 204 that is deflected downward to begin its path through the tissue. The deflecting implement 205 may be withdrawn following implantation, allowing the spring to compress during healing. Compression of the spring will reduce the profile of the implanted coil fastener and can reduce the likelihood of pain induction. Tabs 202 are used for locking a port or other device into the fastener.

Figure 47:
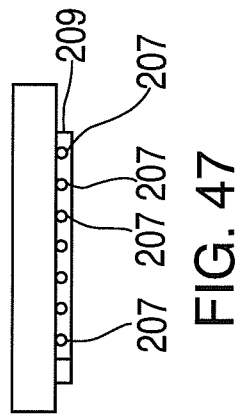
FIG. 47 is a detail view of the horizontal coil fastening system base of FIG. 43.
Figure 43:
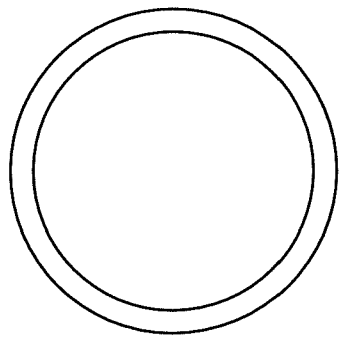
FIG. 43 is a top view of a horizontal coil fastening system base.
Figure 44:
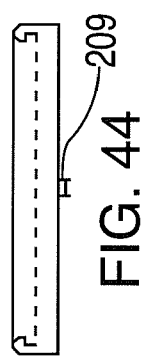
FIG. 44 is a side view of the horizontal coil fastening system base of FIG. 43.
Figure 45:
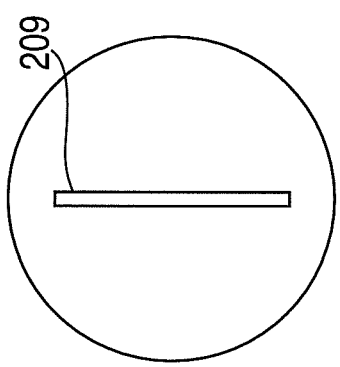
FIG. 45 is a bottom view of the horizontal coil fastening system base of FIG. 43.

FIGS. 43-47 and 55 depict a horizontal coil implantation system. In the horizontal coil system, a metal coil is used horizontally to stitch the port to the tissue. It is well known that such coils can pierce and hold in tissues from their use as mesh tacks in minimally invasive hernia procedures. In this case, the coil travels parallel to the tissue surface instead of perpendicularly, as in the helical coil fasteners described above (see FIG. 55). One example of such a coil is formed of 0.014 inch D wire having a pitch of 0.0100 inch. A small deployment tool 206 with a slotted driver is envisioned to aid in driving the coil 208 through the tissue and the mating holes 207 in the base coil receptacle 209 (see FIGS. 46 and 47). Such holes could be straight holes through a ridge on the bottom of the base (see FIGS. 44, 45 and 47), or curved holes molded into a flat-surfaced base. The coil holes shown in FIG. 47 are shown spaced apart 0.100 inch, the same as the coil pitch, and having a diameter of 0.240 inch. A top view of a base is shown in FIG. 43. It is envisioned that the last hole would be blind, and that the end of the coil would be shaped in a crossbar that could slide over an incline and lock into place, such as into a slot. Desirably, a solid stop for advancement of the coil is provided, and there may be a latch configuration wherein the driver end of the coil catches on the underside of the base. A variation would feature a path for the coil that curves around the port or base edge, facilitating tool access to the coil. This can also be accomplished by varying the flexibility of the coil. A tube can be added to the tool as a shroud in order to keep the rotating coil from picking up strings of tissue before it travels through the holes.

Figure 48:
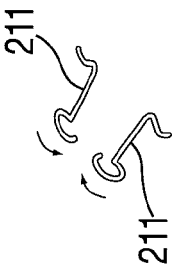
FIG. 48 is a side view of a closed metal loop fastening system incorporated into a device.
Figure 49:
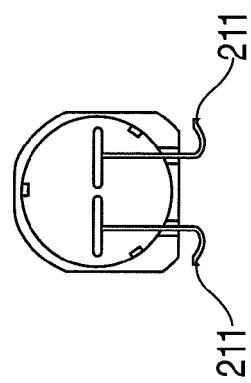
FIG. 49 is a top view of device incorporating the closed metal loop fastening system of FIG. 48.
Figure 51:
FIG. 51 is an elevation view of another closed metal loop system using curved pins or hooks.
Figure 50:
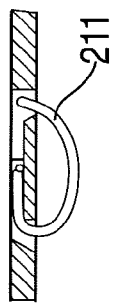
FIG. 50 is a side view of a two-part snap fit fastening system.
Figure 52:
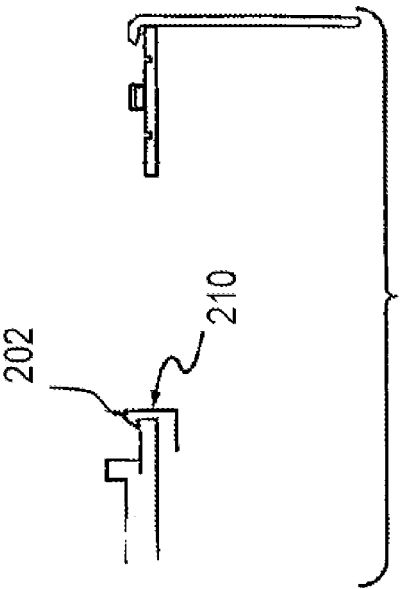
FIG. 52 is a side view of the closed metal loop system using the curved pins or hooks of FIG. 51 incorporated into a device.

FIGS. 48 to 62 depict various embodiments of a metal suture system. This method of port fixation involves the creation of one or multiple closed metal loops below the port base, by using the base itself as a means to close a loop formed by curved metal members 211 (see, e.g. FIGS. 48 and 52). This may be done both with one-piece and two-piece systems, whereby a two-piece system may have a ring 210 that attaches to the port or other device by snap-fitting with tabs 202 as shown in FIG. 50. One embodiment includes a deflection tool to separate the point of the metal member from contact with the base allowing the member tip to begin its path downward through the tissue. This can be a circular disc or the port itself. After the point has traveled some distance, the tool is withdrawn, permitting the curved member to then follow a path intersecting with the base. Likewise, another embodiment includes multiple members curved in two planes, such that rotation of the base affects the creating of multiple loops.

Figure 53:
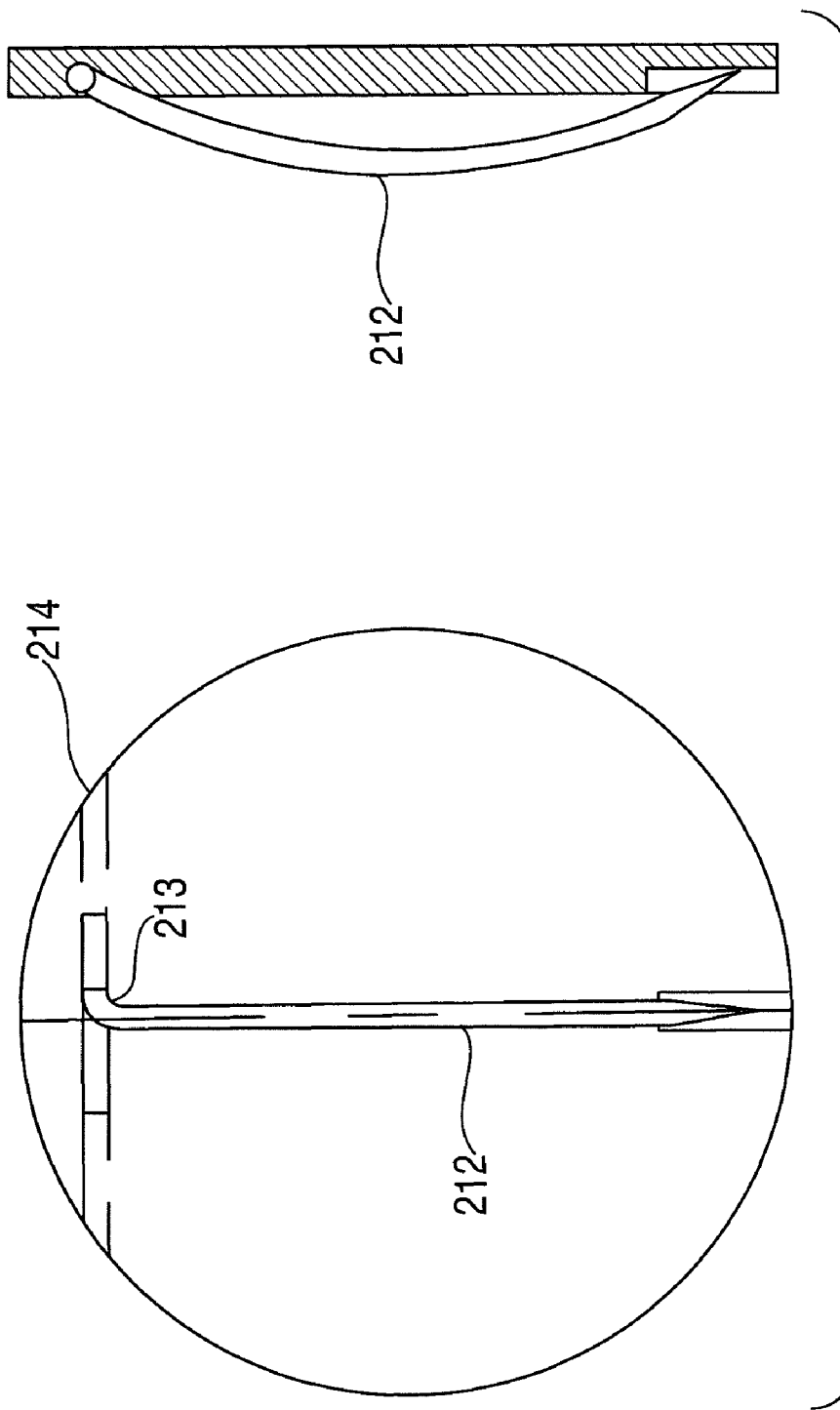
FIG. 53 shows top and side views of a curved pin fastening system incorporated into a device.
Figure 54:
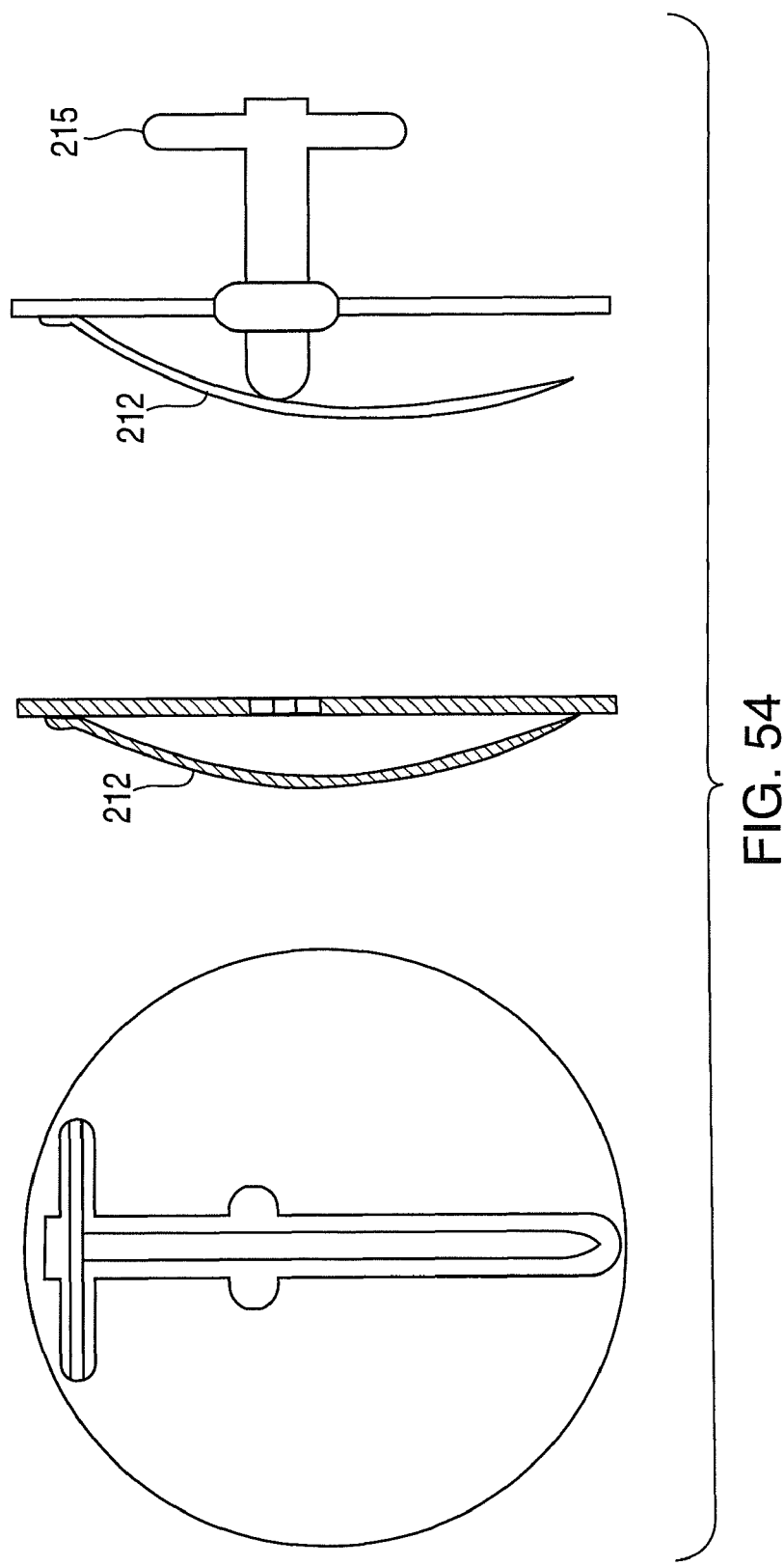
FIG. 54 shows top and side views of another curved pin fastening system incorporated into a device.
Figure 55:
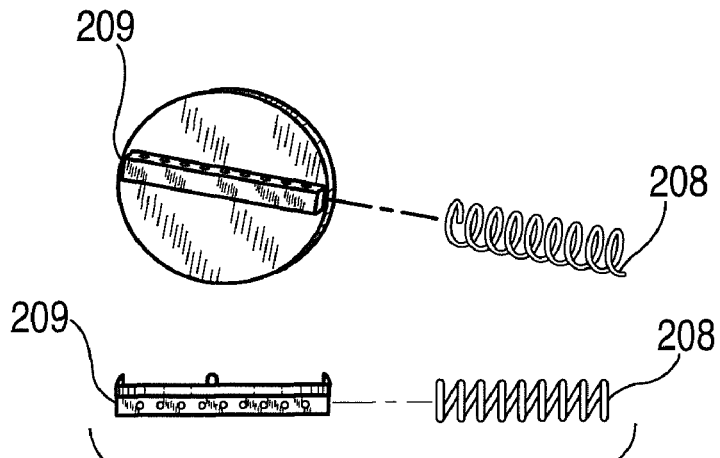
FIG. 55 shows bottom and side views of a spring screw fastening system.

An alternate method to achieve such a loop is with a curved pin 212 (hook or needle) that is inserted through the base after it is in its intended tissue location, as seen in FIGS. 53 and 54. Such a pin by nature follows an arc through the tissue and can easily be directed back to the port base. Such a pin can be made to lock in place after full travel by adding a right angle bend 213 to the pin that snaps into a slot 214 on the base, or other such well-known means. A variation on this theme includes an additional straight section on the end of the pin, parallel to the curved section. A lever arm 215 is used to drive the curved section through the base and to the completion of its intended travel.

Figure 56:
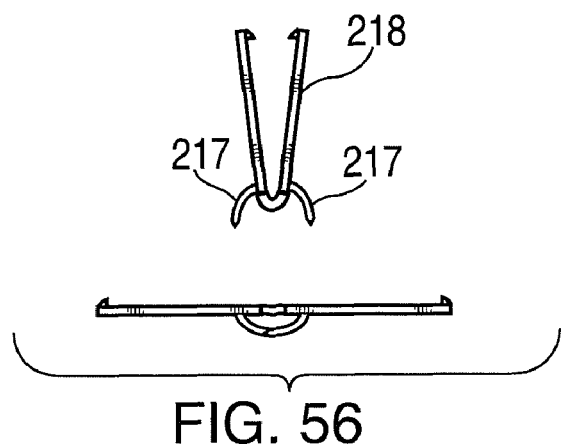
FIG. 56 shows side view of a folding baseplate with curved fasteners in its open and closed positions.
Figure 57:
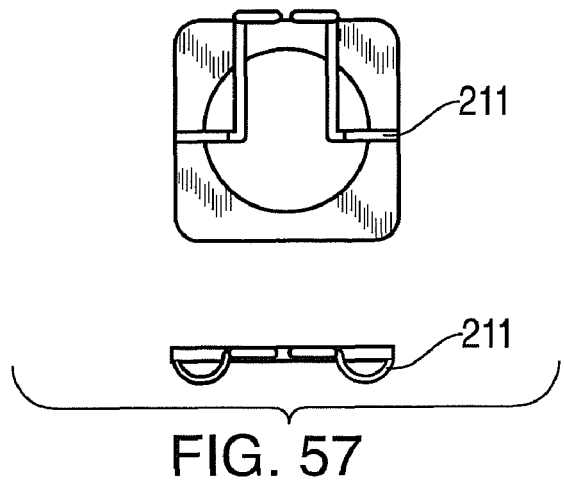
FIG. 57 shows top and side views of rotating hook fasteners incorporated into a device.
Figure 58:
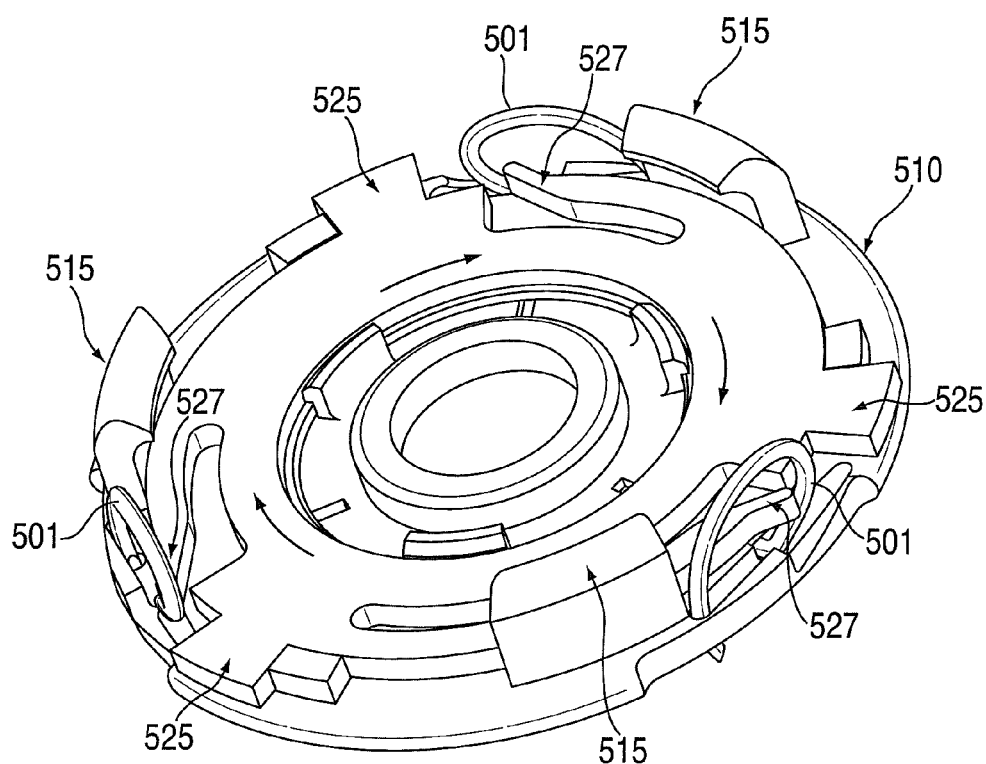
FIG. 58 is a top elevation view of a rotating disc fastening system with fasteners in pre-deployment position.
Figure 59:
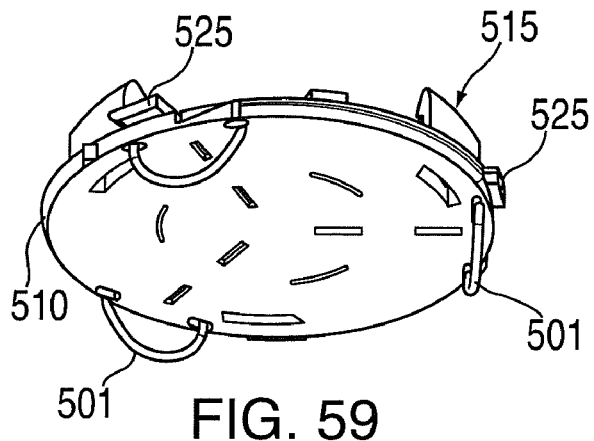
FIG. 59 is a bottom elevation view of the rotating disc fastening system of FIG. 58 with fastener in post-deployment position.
Figure 60:
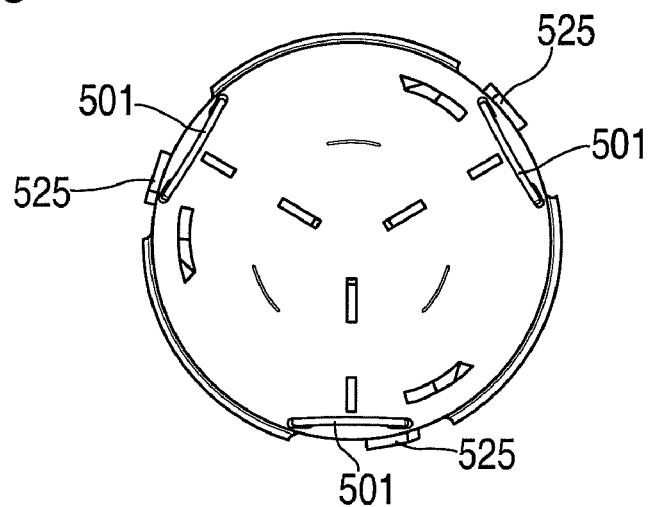
FIG. 60 is a bottom view of the rotating disc fastening system of FIG. 58 with fasteners in post-deployment position.
Figure 61:
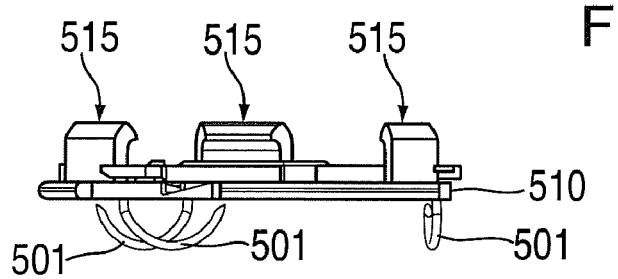
FIG. 61 is a side view of the rotating disc fastening system of FIG. 58 with fasteners partially deployed.
Figure 62:
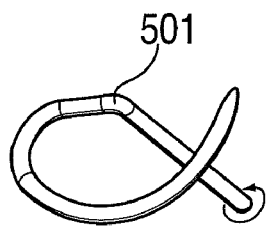
FIG. 62 is an elevation view of the curved fastener of the rotating disc fastening system of FIG. 58 showing the axis of rotation.

In yet another embodiment, a two-piece system may be used wherein the port attaches to a folding baseplate 218 with sharp, curved extensions 217 (see FIG. 56). The folded plate is placed on the tissue with the extensions pointed toward the tissue. When the baseplate is unfolded (flattened) the extensions are driven 90 degrees in a rotary path (see FIG. 56). The port is then snapped to the baseplate, locking the extensions in position. In one embodiment, the points of the extensions would overlap or cross over those from the other half, semi-shielding the points.

FIGS. 58-62 illustrate a preferred rotating disc fastener system. After being placed in its desired location, the device to be implanted is secured to the tissue using a plurality of curved pins or hooks 501 (FIG. 62), the tips of which rotate through an arc and are received back in or near the baseplate 510 at the end of their travel. A disc 520 within the baseplate 510 rotates, thereby causing lever arms 525 to push against curved hooks 501, which in turn rotate about their fixed axis in the baseplate through an arc until the rotational travel of the disc stops. In the fully deployed position (FIGS. 59 and 60), the tips of hooks 501 are preferably received back in baseplate 510 to form a closed loop. Alternatively, the tips may form less than a closed loop. In either case, it is preferable that the rotating disc 520 locks in place at the end of its travel to lock the hooks in place. One-way flexible locking tabs 527 that engage stops 515 or other locking means may be used to lock the hooks in place by preventing backward rotation of the disc. A deployment tool or delivery system such as that described above with reference to FIGS. 5-19 may be used to fasten the device in place. The linear motion of the plunger 22 and slide pusher 24 is converted into rotational motion through a transmission using gearing or other well known means.

Although the invention has been particularly shown and described with reference to certain preferred embodiments, and in particular with reference to an access or injection port, it will be readily appreciated by those of ordinary skill in the art that any number of implantable medical devices may be used with the fastening system of the present invention and that various changes and modifications may be made therein without departing from the spirit and scope of the invention.

What is claimed is:

1. A delivery system and surgically implantable device combination, comprising:
    an implantable device including a fluid reservoir and an upwardly-facing needle-puncturable septum, the device having an outer periphery, wherein the outer periphery comprises a plurality of notches or openings each housing a tissue fastener pivotally attached to the implantable device; and
    a delivery system comprising a proximal handle and a distal cover sized to substantially surround the implantable device, a plunger, a slide pusher and a slide assembly, wherein the slide assembly comprises beams spaced to line up with the notches or openings on the implantable device so as to act on and pivot without bending the tissue fasteners below the implantable device into bodily tissue.

2. The combination of claim 1, wherein the fasteners generate a tactile signal which may be felt in the handle when reaching deployed positions below the implantable device.

3. The combination of claim 1, wherein the fasteners emit an audible signal when reaching deployed positions below the implantable device.

4. The combination of claim 1, wherein the distal cover of the delivery system defines a recess that receives the implantable device therein such that a lower face of the implantable device is exposed, the cover and recess being oriented to extend down over the implantable device generally vertically, the delivery system including a shaft extending upward at an angle to the vertical from the distal cover to the proximal handle.

5. The combination of claim 1, wherein the fasteners comprise curved hooks distributed evenly around the implantable device.

6. The combination of claim 5, wherein sharp tips of the curved hooks rotate through an arc and are received back in or near a lower face of the implantable device in deployed positions.

7. The combination of claim 1, wherein the implantable device comprises an implantable injection port further comprising a housing which surrounds the reservoir, the port further including an outlet conduit extending through a side wall of the housing from the reservoir.

8. A delivery system and surgically implantable device combination, comprising:
    an implantable device including a fluid reservoir and an upwardly-facing needle-puncturable septum, the device having tissue fasteners pivotally attached thereto and acted on by a rotating disc in the device; and
    a delivery system comprising a proximal handle and a distal cover sized to substantially surround and act on the implantable device, the delivery system further including a transmission that converts linear motion of a plunger in the handle into rotational motion of the disc to deploy the tissue fasteners below the implantable device into bodily tissue.

9. The combination of claim 8, wherein the fasteners generate a tactile signal which may be felt in the handle when reaching deployed positions below the implantable device.

10. The combination of claim 8, wherein the fasteners emit an audible signal when reaching deployed positions below the implantable device.

11. The combination of claim 8, wherein the fasteners comprise curved hooks distributed evenly around the implantable device.

12. The combination of claim 11, wherein sharp tips of the curved hooks rotate through an arc and are received back in or near a lower face of the implantable device in deployed positions.

13. The combination of claim 8, wherein the implantable device comprises an implantable injection port further comprising a housing which surrounds the reservoir, the port further including an outlet conduit extending through a side wall of the housing from the reservoir.

14. The combination of claim 8, wherein the distal cover of the delivery system defines a recess that receives the implantable device therein such that a lower face of the implantable device is exposed, the cover and recess being oriented to extend down over the implantable device generally vertically, the delivery system including a shaft extending upward at an angle to the vertical from the distal cover to the proximal handle.

15. The combination of claim 14, wherein the proximal handle of the delivery system has a palm-grip actuator angled with respect to the shaft, the palm-grip actuator including a lever connected to the transmission and pivotally mounted with respect to a housing portion to enable an operator to squeeze the lever and housing portion together in his/her palm and deploy the fasteners.

16. The combination of claim 15, wherein the delivery system includes a plunger mounted to slide linearly through a portion of the shaft and displaced by the lever of the palm-grip actuator.

* * * * *

UNITED STATES PATENT AND TRADEMARK OFFICE
CERTIFICATE OF CORRECTION

PATENT NO.        : 8,007,465 B2                                              Page 1 of 1
APPLICATION NO.   : 12/488496
DATED             : August 30, 2011
INVENTOR(S)       : Birk et al.

It is certified that error appears in the above-identified patent and that said Letters Patent is hereby corrected as shown below:

On the first page, in field (75), in "Inventors", in column 1, line 1, delete "A. Birk," and insert -- Birk, --, therefor.

On the first page, in field (75), in "Inventors", in column 1, line 3, delete "Hoyt," and insert -- Hoyt Jr., --, therefor.

In column 5, line 44, delete "MS" and insert -- $M_S$ --, therefor.

In column 12, line 28, delete "base plate." and insert -- baseplate. --, therefor.

Signed and Sealed this
Nineteenth Day of June, 2012

David J. Kappos
*Director of the United States Patent and Trademark Office*